(12) United States Patent
Klaveness et al.

(10) Patent No.: US 7,182,934 B2
(45) Date of Patent: Feb. 27, 2007

(54) CONTRAST AGENTS

(75) Inventors: Jo Klaveness, Oslo (NO); Anne Naevestad, Oslo (NO); Alan Cuthbertson, Oslo (NO)

(73) Assignee: GE Healthcare AS, Oslo (NO)

( * ) Notice: Subject to any disclaimer, the term of this patent is extended or adjusted under 35 U.S.C. 154(b) by 0 days.

(21) Appl. No.: 11/108,598

(22) Filed: Apr. 18, 2005

(65) Prior Publication Data

US 2005/0201930 A1 Sep. 15, 2005

Related U.S. Application Data

(60) Division of application No. 10/370,092, filed on Feb. 21, 2003, now Pat. No. 6,921,525, which is a division of application No. 09/785,177, filed on Feb. 20, 2001, now Pat. No. 6,524,552, which is a division of application No. 09/300,434, filed on Apr. 28, 1999, now Pat. No. 6,264,914, which is a continuation of application No. PCT/GB97/02956, filed on Oct. 28, 1997.

(60) Provisional application No. 60/058,247, filed on Sep. 9, 1997.

(30) Foreign Application Priority Data

| Oct. 28, 1996 | (GB) | ................................. 9622364.9 |
| Oct. 28, 1996 | (GB) | ................................. 9622365.6 |
| Oct. 28, 1996 | (GB) | ................................. 9622366.4 |
| Oct. 28, 1996 | (GB) | ................................. 9622367.2 |
| Oct. 28, 1996 | (GB) | ................................. 9622368.0 |
| Oct. 28, 1996 | (GB) | ................................. 9622369.8 |
| Jan. 15, 1997 | (GB) | ................................. 9700699.3 |
| Feb. 4, 1997 | (GB) | ................................. 9702195.0 |
| Mar. 24, 1997 | (GB) | ................................. 9706063.6 |

(51) Int. Cl.
*A61K 49/00* (2006.01)

(52) U.S. Cl. ...................... 424/9.1; 424/1.11; 424/1.65; 424/9.3; 424/9.5; 544/224

(58) Field of Classification Search ............... 424/1.11, 424/1.65, 1.69, 9.1, 9.3, 9.4, 9.5, 9.6, 9.7, 424/9.8; 544/224

See application file for complete search history.

(56) References Cited

U.S. PATENT DOCUMENTS

| 6,264,914 B1 * | 7/2001 | Klaveness et al. ......... 424/1.65 |
| 6,524,552 B2 * | 2/2003 | Klaveness et al. ......... 424/1.85 |
| 6,921,525 B2 * | 7/2005 | Klaveness et al. ......... 424/1.65 |

* cited by examiner

*Primary Examiner*—Dameron L. Jones
(74) *Attorney, Agent, or Firm*—Li Cai

(57) ABSTRACT

The invention provides a composition of matter of formula I $$V\text{-}L\text{-}R \quad (I)$$

Figure 1:
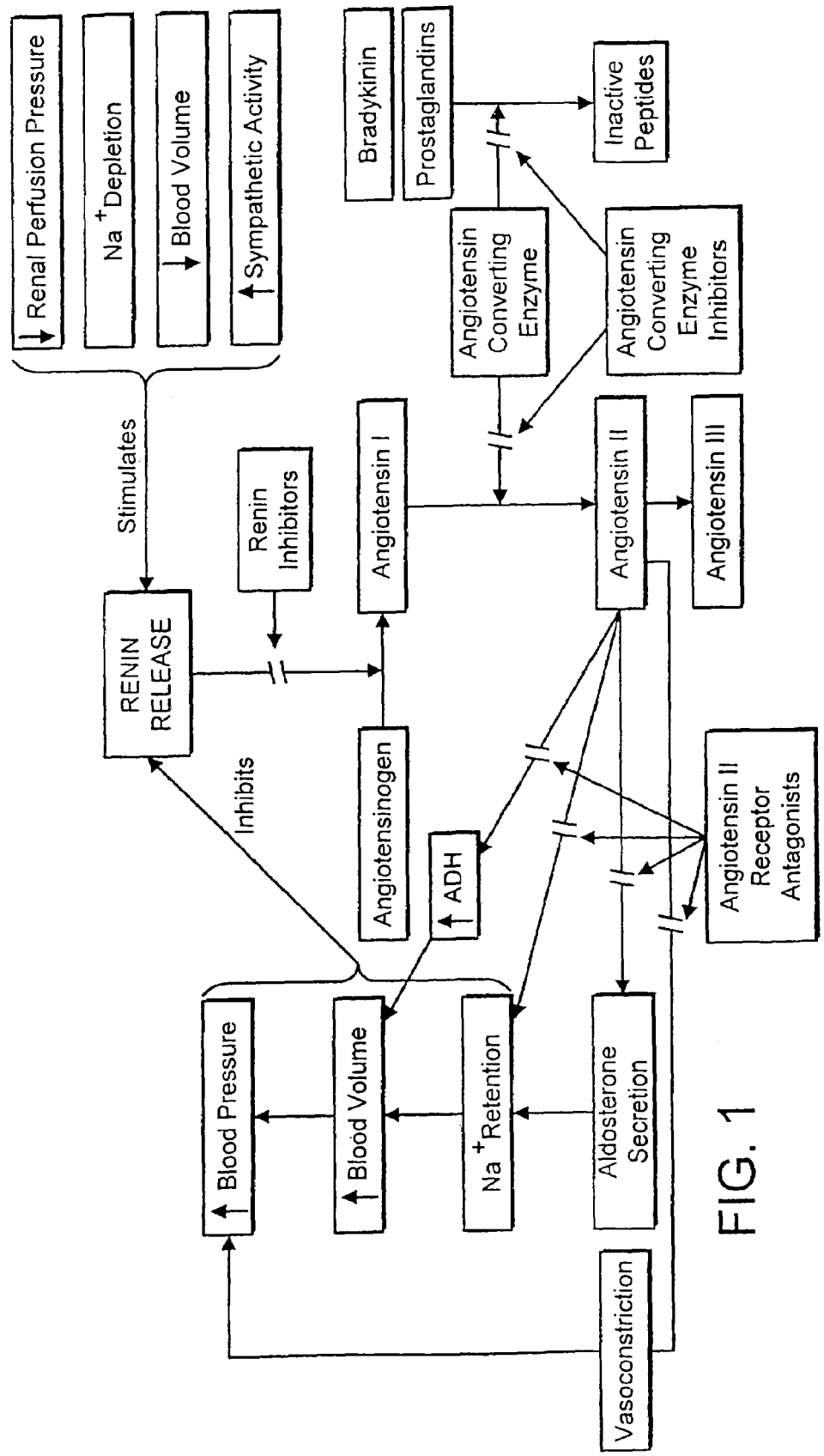

where V is an organic group having binding affinity for an angiotensin II receptor site, L is a linker moiety or a bond, and R is a moiety detectable in in vivo imaging of a human or animal body, with the provisos that where V is angiotensin or a peptidic angiotensin derivative or analog then V-L-R is other than a non-metal radionuclide substituted peptide (eg $^{125}$I substituted angiotensin II) and L-V is other than simply a peptide with a chelating agent amide bonded to a side chain thereof. This composition of matter may be used to image cardiovascular diseases and disorders.

5 Claims, 1 Drawing Sheet

CONTRAST AGENTS

This application is a division of U.S. application Ser. No. 10/370,092 filed Feb. 21, 2003 now U.S. Pat. No. 6,921,525 which is a divisional of application Ser. No. 09/785,177, filed Feb. 20, 2001, now U.S. Pat. No. 6,524,552, which is a divisional of application Ser. No. 09/300,434, filed Apr. 28, 1999, now U.S. Pat. No. 6,264,914, which is a continuation of PCT/GB97/02956, filed Oct. 28, 1997, which claims benefit of provisional application No. 60/058,247 filed Sep. 9, 1997 the entire disclosure of which is hereby incorporated by reference.

This invention relates to diagnostic imaging techniques in which a disease state may be imaged using a targeted contrast agent and to targeted contrast agents suitable for use in such techniques. More particularly the invention relates to the use of such contrast agents in which the targeting vector binds to angiotensin II receptors.

Angiotension II (hereinafter AII) is an octapeptide (Asp-Arg-Val-Tyr-Ile-His-Pro-Phe) which is the primary active species in the renin-angiotensin aldosterone system (the RAS system) which regulates blood pressure and electrolyte and water balance. The RAS system is illustrated schematically in FIG. 1 hereto which is based on FIG. 1 in the article by Foote et al. in Ann. Pharmacother. 27: 1495–1503 (1993).

AII exerts its biological effects via interaction with specific receptors present in many tissues in the human or animal body (eg. blood vessels, heart, brain, liver, kidney, uterus and ovary). While one of its major effects is to promote vasoconstriction, AII has several other effects that lead to increased blood pressure and sodium retention. Thus, for example, in response to stimulation of AII receptors in the adrenal cortex, aldosterone is released and this stimulates sodium and water retention and potassium excretion in the distal tubules and cortical collecting ducts of the kidney. AII also has a direct effect on the kidney including glomerular hypertrophy and increased proximal tubule sodium reabsorption. Furthermore, AII acts centrally to stimulate thirst and enhance antidiuretic hormone release thereby leading to increased intravascular volume.

Accordingly, suppression of AII's effects has been used therapeutically, for example in the management of hypertension and congestive heart failure. This has been achieved in a number of ways: by the use of renin inhibitors which block the conversion of angiotensinogen to angiotensin I (the precursor to AII); by the use of angiotensin converting enzyme (ACE) inhibitors that block the conversion of angiotensin I to AII (and also block bioconversion of bradykinin and prostaglandins); by the use of anti-AII-antibodies; and by the use of AII-receptor antagonists.

It has been found that different types of AII receptors (binding sites) exist within the body and that AII binding has different effects at different binding sites. Thus the AT1 receptor mediates the major cardiovascular action of the RAS and is inhibited by the AII-receptor antagonists Losartan and DTT, while the other major receptor family, AT2, is inhibited by PD 123177 and its structural analogs. Other receptors for AII besides AT1 and AT2 are known and are generally referred to as $AT_{atypical}$ (see Kang et al., Am. Heart J. 127: 1388–1401 (1994)).

It has now been found that it is possible to image AII receptor sites in vivo using targeted contrast agents in which the targeting vector has affinity for AII-receptor sites. The AII receptors are generally located within the cardiovascular system and are accessible to such contrast agents when they are administered into the blood stream. Accordingly, using such targeted contrast agents it is possible to detect diseases and disorders such as heart failure, atherosclerosis and restricted blood flow, as well as other vascular diseases and disorders, and also to monitor the progression of treatment for such diseases and disorders.

Viewed from one aspect therefore the invention provides a composition of matter of formula I $$V-L-R \quad \quad (I)$$

where V is an organic group having binding affinity for an angiotensin II receptor site, L is a linker moiety or a bond, and R is a moiety detectable in in vivo imaging of a human or animal body, with the provisos that where V is angiotensin or a peptidic angiotensin derivative or analog then V-L-R is other than a non-metal radionuclide substituted peptide (eg $^{125}I$ substituted angiotensin II) and L-V is other than simply a peptide with a chelating agent amide bonded to a side chain thereof.

Preferably where R is a radionuclide it is an iodine bonded directly or indirectly to V or it is a metal ion chelated by a chelant group in L, and/or it is separable from V by biodegradation of an organic linker group L. (It should be noted that hydrogen radionuclides, while detectable in vitro, will not satisfy the requirement that R be detectable in in vivo imaging).

Preferably where V is angiotensin then R is not a metal ion.

In many instances, the composition of matter of formula I will be a characterisable compound. In others it may be a combination of compounds bonded or otherwise associated, eg. conjugated, with each other. For convenience sake, the composition of matter will be referred to hereinafter as an agent.

Viewed from a further aspect the invention provides a pharmaceutical composition comprising an effective amount (eg. an amount effective to enhance image contrast in in vivo imaging) of an agent of formula I together with at least one pharmaceutically effective carrier or excipient.

Viewed from a still further aspect the invention provides the use of an agent of formula I for the manufacture of a contrast medium for use in a method of diagnosis involving administration of said contrast medium to an animate subject and generation of an image of at least part of said subject.

Viewed from a still further aspect the invention provides a method of generating an image of an animate human or non-human (preferably mammalian or avian) animal subject involving administering a contrast agent to said subject and generating an image of at least a part of said subject to which said contrast agent has distributed, eg. by X-ray, MR, ultrasound, scintigraphic, PET, SPECT, electrical impedance, light or magnetometric imaging modalities, characterised in that as said contrast agent is used an agent of formula I.

Viewed from a further aspect the invention provides a method of monitoring the effect of treatment of a human or non-human animal subject with a drug to combat or provoke effects associated with angiotensin II, said method involving administering to said subject an agent of formula I and detecting the uptake of said agent by angiotensin II receptors, said administration and detection optionally but preferably being effected repeatedly, eg. before, during and after treatment with said drug.

Viewed from a yet further aspect the invention provides a process for the preparation of an agent of formula I, said process comprising conjugating (i) an organic compound having binding affinity for an AII receptor to (ii) a compound detectable in a diagnostic imaging procedure or a chelant compound and if necessary metallating chelant groups in the resultant conjugate with a metal ion detectable in a diagnostic imaging procedure.

The agents of formula I have three characteristic components: a vector (V); a linker (L); and a reporter (R). The vector must have the ability to target the compound to AII receptors, the reporter must be detectable in an in vivo diagnostic imaging procedure; and the linker must couple vector to reporter, at least until the imaging procedure has been completed.

Vectors

As the vector, one may use any compound having affinity for AII receptors. This may be a peptide (such as AII itself or an analog such as saralasin (Sar-Arg-Val-Tyr-Val-His-Pro-β-Ala)) or a non-peptide such as losartan or PD-123177, although non-peptides are preferred. Similarly, the vector may be a compound (such as losartan) which has more pronounced affinity for one type of AII-receptor than for other types, or a compound (such as AII itself) which has general affinity for all AII receptors. Compounds having more pronounced affinity for particular types of AII receptors (such as AT1 or AT2) will generally be preferred.

Preferably the agent is a compound which does not elicit any unacceptable biological response, particularly compounds which act as AII receptor antagonists and do not elicit the responses associated with AII itself, especially the blood pressure modifying responses. However, biological responses may if desired be modified by administration of a therapeutic agent, eg. before, at the same time or after administration of the agent of formula I.

Among peptidic vectors, oligopeptides having the motif Arg-Val-Tyr-Ile-His-Pro or an analogous motif in which any one of the five amino acid residues may be varied either individually or in concert with structural or functional isosteres such that the structural or functional motif is conserved so permitting effective interaction with angiotensin II receptor sites. By way of example, the motifs Arg-Val-Tyr*-XX-His-Pro (where Tyr* is an optionally modified Tyr, eg. Me-Tyr and XX is an amino acid, eg. Ile or Val) are preferred, for example AII and more particularly saralesin and sarmesin. However where AII or such close angiotensin analogs are used as the vector, it may be desirable to utilize linker-reporter combinations other than metallated chelants (eg. including a radionuclide or paramagnetic metal ion) bound directly to the peptidic structure; thus it may be desirable to use a non-metal radionuclide reporter, or to use a particulate reporter.

Other suitable oligopeptide vectors can readily be determined using phage display, combinational chemistry (both peptidic and non-peptidic combinational chemistry), HTS (high throughput synthesis) and CAM.D techniques.

Among non-peptidic vectors, losartan and PD 123177 are preferred. Other suitable non-peptide vectors include heterocyclic compounds (such as imidazoles, condensed imidazoles, xanthines and pyridones). Examples of suitable non-peptidic vectors are given in WO-91/17148, U.S. Pat. No. 4,355,040, WO-91/18888, WO-91/19715, WO-91/15209, EP-A-420237, EP-A-459136 and U.S. Pat. No. 5,338,744. The development of appropriate non-peptidic AII receptor antagonists is discussed for example by Timmermans et al., in TiPS 12: 55–62 (1991) and Pharm. Rev. 45: 205–251 (1993) and by van Meel et al. in Arzneim-Forsch./Drug Res. 43: 242–246 (1993).

Suitable non-peptidic vectors will generally contain a 5 or 6 membered unsaturated $N_1$, $N_2$ or $N_3$ heterocyclic ring, optionally carrying a condensed 5 or 6 membered unsaturated, optionally heterocyclic, ring and optionally carrying pendent groups which comprise one or more (eg. 1, 2 or 3) 5 or 6 membered homo or heterocyclic aryl groups, eg. aryl-methyl-biphenyl tetrazoles. Examples include DuP 753, L-158809, SR-47436, GR 117289, SKF 108566, BIBS 39, BIBS 222, ExP 3892 and CGP 48933.

Thus the vector compound may for example be a compound of formula II

wherein $R_1$ and $R_2$ are carboxy groups or $C_{1-6}$ alkyl groups optionally substituted by oxa, oxo, phenyl, amino, carboxyl or hydroxy groups or $R_1$ may additionally represent an oxo group, and $R_3$ and $R_4$ are methyl biphenyl carboxyl or methyl biphenyl tetrazole groups or $C_{1-6}$ alkyl groups optionally substituted by oxa, oxo, phenyl, amino, carboxyl or hydroxy groups, $R_4$ being present only when $R_1$ is oxo, preferably with one of $R_3$ and $R_4$ representing a biphenyl containing group and with one of the groups $R_1$, $R_2$, $R_3$ and $R_4$ representing an alkyl group substituted by oxa, oxo, phenyl, amino, carboxyl or hydroxy groups.

In such compounds, the amino, hydroxy, carbonyl or carboxy functions may readily be used to conjugate the vector to the reporter.

Thus examples of such triazole vectors include

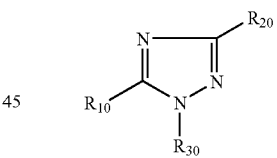

$R_{31}$ where $R_{30}$ is $CH_2$—O—O $R_{31}$ is COOH, tetrazol-5-yl, $NH_2SO_2CF_3$, $SO_2NHCO$-phenyl, $SO_2NHCO$-cyclopropyl, and $R_{10}$ and $R_{20}$ are

| $R_{10}$ | $R_{20}$ |
|---|---|
| n Bu | $NH_2CH_2$ |
| $NH_2CH_2$ | nBu |
| n Bu | 3-hydroxypropyl |
| 3-hydroxypropyl | n-Bu |
| n Bu | COOH |
| n Bu | $CH_3CO$ |
| n Bu | 2-carboxyethyl |
| 2-carboxyethyl | nBu |
| 3-aminopropyl | nBu |
| nBu | 3-aminopropyl |

-continued

| $R_{10}$ | $R_{20}$ |
|---|---|
| 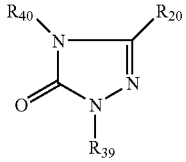 | |

$R_{31}$ where $R_{40}$ is $CH_2$—O—O, $R_{31}$ is as defined above and $R_{20}$ and $R_{39}$ are

| $R_{39}$ | $R_{20}$ |
|---|---|
| phenyl-CHOHCH$_2$ | nBu |
| carboxymethyl | nBu |
| 2-carboxymethoxy-2-phenylethyl | nBu |
| 2(2,4-dimethoxyphenyl)-2-hydroxyethyl | nBu |
| 4-carboxybutyl | nBu |

Similarly the vector may be a compound of formula III

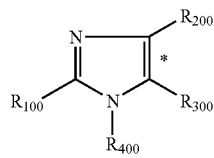  (III)

where the double bond marked with an asterisk is optionally replaced by a single bond; $R_{100}$ is a hydrogen atom, a phenyl group optionally substituted by at least one hydroxy or amino group, or a $C_{1-6}$ alkyl group optionally substituted by a hydroxy group or optionally attached via an oxygen, sulphur or nitrogen; $R_{400}$ is an arylmethyl group, e.g a methylbiphenyl (optionally substituted on a phenyl ring by an acid function, e.g. a carboxyl, or an ester thereof, e.g. a ($C_{1-6}$ alkoxy)-carbonyl group) or methylbiphenyltetrazole group attached via the methyl group, or an optionally $C_{1-6}$ alkyl-, amino- and/or hydroxy-substituted benzyl group; $R_{300}$ is a carboxymethyl group or an optionally hydroxy-substituted $C_{1-6}$ alkyl group, e.g. a hydroxy-methyl group, and $R_{200}$ is chlorine or $R_{300}$ and $R_{200}$ together with the intervening carbons form a fused 6-membered carbocyclic or heterocyclic aromatic ring (containing 0, 1 or 2 ring nitrogens) optionally substituted at a ring carbon by a hydroxy, carboxyl, $C_{1-6}$ alkyl or acyloxy group (wherein the acyl group comprises a $C_{1-6}$ alkyl, phenyl, or benzyl group) or at a ring nitrogen by an acyl group (eg. a $C_{1-6}$ alkyl carbonyl group optionally substituted by phenyl groups). Preferably at least one of $R_{100}$, $R_{200}$, $R_{300}$ and $R_{400}$ contains a hydroxy, amino, thiol, mercapto, aldehydic, ketonic, or carboxylic acid group, or a multiple bond (eg. a C=C bond) or any other functional group which can be used for attachment of the vector to the reporter moiety.

Thus by way of example, the compound of formula III may be of formula

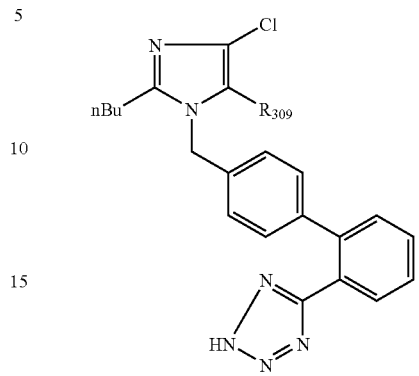

where $R_{309}$ is hydroxymethyl or carboxy, or of formula

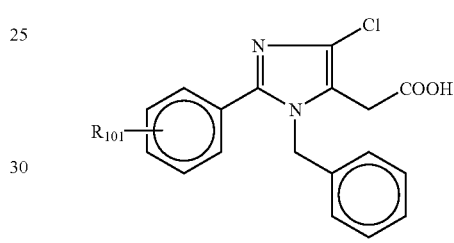

where $R_{101}$-phenyl- is 3,4-dihydroxyphenyl, 4-aminophenyl or 2-hydroxyphenyl, or of formula

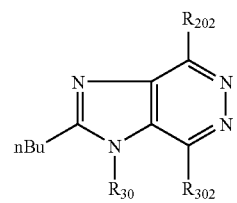

where $R_{30}$ is as defined above, eg. methyl-biphenyl tetrazole or methylbiphenylcarboxyl, and $R_{202}$ and $R_{302}$ are as follows:

| $R_{202}$ | $R_{302}$ |
|---|---|
| OH | H |
| nPr | OH |
| OH | OH |
| OH | tBuCOO |
| phenylCOO | OH |
| tBuCOO | OH |
| benzylCOO | OH |

Alternatively the vector of formula III may be for example of formula

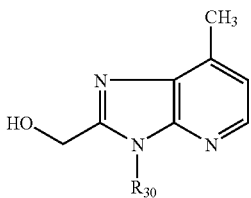

where $R_{30}$ is as defined above, or of formula

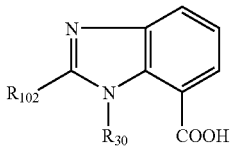

where $R_{30}$ is as defined above and $R_{102}$ is $C_{1-3}$ alkyl attached via O, S or NH, or of formula

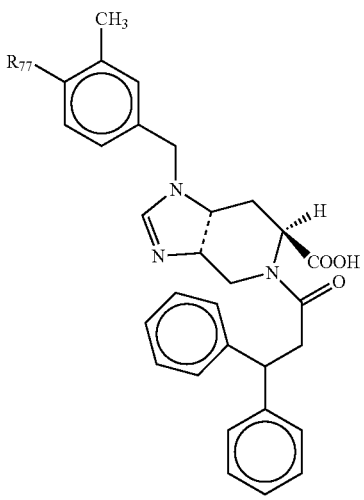

where $R_{77}$ is hydroxy or amino and the dashed bond is a double or a single bond, preferably a double bond where $R_{77}$ is amino and a single bond where $R_{77}$ is hydroxy.

Moreover the vector may be a compound of formula IV

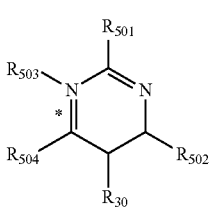

(IV)

where $R_{501}$ is an optionally fluorinated $C_{1-6}$ alkyl group, $R_{504}$ is an optionally fluorinated $C_{1-6}$ alkyl group, $R_{502}$ is a carboxy, hydroxy-$C_{1-6}$ alkyl or CHO group; or the double bond marked with an asterisk is replaced by a single bond and $R_{504}$ is an =O or =$NR_{505}$ (where $R_{505}$ is $C_{1-6}$ alkyl) group, $R_{502}$ is an optionally fluorinated $C_{1-6}$ alkyl group and $R_{503}$ is a carboxyphenyl group; and $R_{30}$ is as defined above (eg. where $R_{31}$ is tetrazol-5-yl, $NH_2SO_2CF_3$, $SO_2NHCO$—cyclopropyl or $SO_2NHCO$-phenyl).

Thus for example the vector of formula IV may be of formula

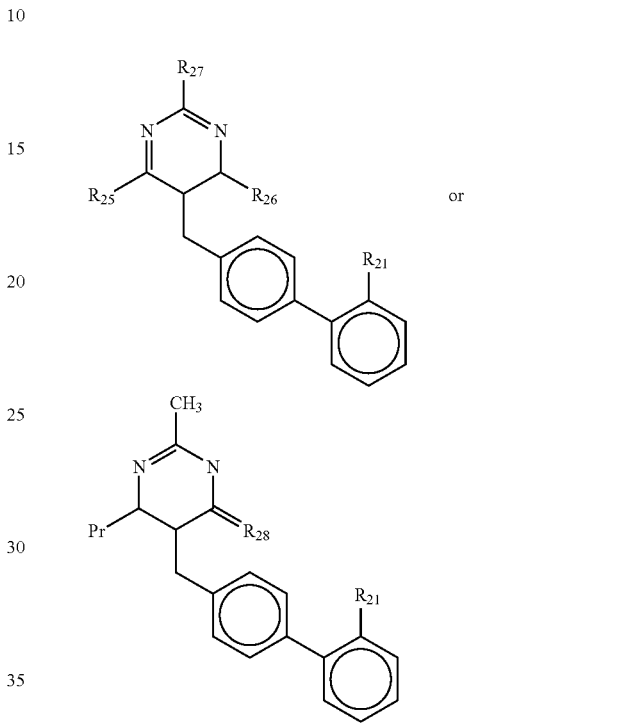

where $R_{27}$ is methyl or $C_2F_5$,
$R_{26}$ is COOH, CHO or $CH_2OH$,
$R_{25}$ is butyl or propyl,
$R_{28}$ is =O or =$NCH_3$, and
$R_{21}$ is tetrazol-5-yl, $NH_2SO_2CF_3$, $SO_2NHCO$-cyclopropyl or $SO_2NHCO$-phenyl.

Other compounds suitable for use as vectors include compounds such as those described in WO 92/18529, U.S. Pat. No. 5,156,977, EP-A-435827, EP-A-424317, EP-A-420237, EP-A-426021, WO 92/09556, WO 91/19715, WO 91/18888, WO 91/17148, EP-A-446062, WO 92/09563, WO 91/15479, WO 91/15209, EP-A-459136, EP-A-445811, EP-A-442473, EP-A-430300, U.S. Pat. No. 4,355,040, U.S. Pat. No. 4,340,598 and U.S. Pat. No. 5,338,744.

The vectors of formulae II to IV may be prepared by the techniques described in the patent publications referred to herein.

CAM-D and other candidate identification and evaluation techniques as mentioned above can also be used to find or assess further candidate non-peptide vectors.

Thus it is also possible to obtain molecules that bind specifically to angiotensin II receptors by direct screening of molecular libraries. For example, phage libraries displaying small peptides could be used for such selection. The selection may be made by simply mixing the receptors and the phage display library and eluting the phages binding to the receptors. If desired, the selection can be done under "physiological conditions" (e.g. in blood) to eliminate peptides which cross-react with blood components. Binding moieties identified in this way may be coupled (by chemical conjugation or via peptide synthesis, or at the DNA-level for recombinant vectors) to a linker molecule, constituting a general tool for attaching any vector molecule to the reporter.

Vector molecules may be generated from combinatorial libraries without necessarily knowing the exact molecular target, by functionally selecting (in vitro, ex vivo or in vivo) for molecules binding to the region/structure to be imaged.

Vectors from Combinatorial Libraries

| Vector type | Target | Comments/areas of use |
|---|---|---|
| Antibodies with structure determined during generation process | Any of above targets - or may be unknown when make functional selection of vector binding to AII receptors | Any diseased or normal structure of interest having AII receptors |
| Peptides with sequence determined during generation process | Any of above targets - or may be unknown when make functional selection of vector binding to AII receptors | Any diseased or normal structure of interest having AII receptors |
| Oligonucleotides with sequence determined during generation process | Any of above targets - or may be unknown when make functional selection of vector binding to AII receptors | Any diseased or normal structure of interest having AII receptors |
| Modifications of oligos obtained as above | Any of above targets - or may be unknown when make functional selection of vector binding to AII receptors | Any diseased or normal structure of interest having AII receptors |
| Other chemicals with structure determined during generation process | Any of above targets - or may be unknown when make functional selection of vector binding to AII receptors | Any diseased or normal structure of interest having AII receptors |

(see for example: Abelson (Ed), Meth. Enzymol. 267 Combinatorial Chemistry, Academic Press, San Diego, 1996; Cortese (Ed), Combinatorial Libraries: Synthesis, Screening and Application Potential, Walter de Gruyter, Berlin, 1996; and Wu, Nat. Biotech. 14: 429–431 (1996)).

The vector moiety in the agents of formula I will preferably have a formation constant for R-L-V: angiotensin II receptor site conjugation of at least 100.

As mentioned above, the agents of formula I comprise vector, linker and reporter moieties. A linker moiety may serve to link one vector to one reporter; alternatively it may link together more than vector and/or more than one reporter. Likewise a reporter or a vector may be linked to more than one linker. Use in this way of a plurality of reporters (eg. several linker-reporter moieties attached to one vector or several reporters attached to one linker itself attached to one vector) may enable the detectability of the contrast agent to be increased (eg. by increasing its radioopacity, echogenicity or relaxivity) or may enable it to be detected in more than one imaging modality. Use in this way of a plurality of vectors may increase the targeting efficiency of the contrast agent or may make the contrast agent able to target more than one site, eg. different receptors for an agent which has receptor heterogeneity. Thus for example the agent of formula I may include vector moieties with affinity sites other than angiotensin receptors, eg. with affinities for cell surfaces on body duct wall surfaces.

Accordingly, the agent may include vectors such as antibody fragments and oligopeptides, eg. containing RGD or analogous cell surface binding peptide motifs (for example as described in EP-A-422937 and EP-A-422938 (Merck)) or other vectors as described in GB 9700699.3.

Such extra vectors may also be selected from any of the molecules that naturally concentrate in a selected target organ, tissue, cell or group of cells, or other location in a mammalian body, in vivo. These can include amino acids, oligopeptides (e.g. hexapeptides), molecular recognition units (MRU's), single chain antibodies (SCA's), proteins, non-peptide organic molecules, Fab fragments, and antibodies. Examples of site-directed molecules include polysaccharides (e.g. CCK and hexapeptides), proteins (such as lectins, asialofetuin, polyclonal IgG, blood clotting proteins (e.g. hirudin), lipoproteins and glycoproteins), hormones, growth factors, clotting factors (such as PF4), polymerized fibrin fragments (e.g., $E_1$), serum amyloid precursor (SAP) proteins, low density lipoprotein (LDL) precursors, serum albumin, surface proteins of intact red blood cells, receptor binding molecules such as estrogens, liver-specific proteins/polymers such as galactosyl-neoglycoalbumin (NGA) (see Vera et al. in Radiology 151: 191 (1984)) N-(2-hydroxypropyl)methacrylamide (HMPA) copolymers with varying numbers of bound galactosamines (see Duncan et al., Biochim. Biophys. Acta 880:62 (1986)), and allyl and 6-aminohexyl glycosides (see Wong et al., Carbo. Res. 170:27 (1987)), and fibrinogen. The site-directed protein can also be an antibody. The choice of antibody, particularly the antigen specificity of the antibody, will depend on the particular intended target site for the agent. Monoclonal antibodies are preferred over polyclonal antibodies. Preparation of antibodies that react with a desired antigen is well known. Antibody preparations are available commercially from a variety of sources. Fibrin fragment $E_1$ can be prepared as described by Olexa et al. in J. Biol. Chem. 254:4925 (1979). Preparation of LDL precursors and SAP proteins is described by de Beer et al. in J. Immunol. Methods 50:17 (1982). The above described articles are incorporated herein by reference in their entirety.

It is especially preferred that such extra vectors should bind so as to slow but not prevent the motion of the agent in the blood stream and to anchor it in place when it is bound to an AII receptor site.

Linker

The linker component of the contrast agent is at its simplest a bond between the vector and reporter moieties. More generally however the linker will provide a mono- or multi-molecular skeleton covalently or non-covalently linking one or more vectors to one or more reporters, eg. a linear, cyclic, branched or reticulate molecular skeleton, or a molecular aggregate, with in-built or pendant groups which bind covalently or non-covalently, eg. coordinatively, with the vector and reporter moieties or which encapsulate, entrap or anchor such moieties.

Thus linking of a reporter unit to a desired vector may be achieved by covalent or non-covalent means, usually involving interaction with one or more functional groups located on the reporter and/or vector. Examples of chemically reactive functional groups which may be employed for this purpose include amino, hydroxyl, sulfhydryl, carboxyl, and carbonyl groups, as well as carbohydrate groups, vicinidial diols, thioethers, 2-aminoalcohols, 2-aminothiols, guanidinyl, imidazolyl and phenolic groups.

Covalent coupling of reporter and vector may therefore be effected using linking agents containing reactive moities capable of reaction with such functional groups. Examples of reactive moieties capable of reaction with sulfhydryl groups include α-haloacetyl compounds of the type X—CH$_2$CO— (where X=Br, Cl or I), which show particular reactivity for sulfhydryl groups but which can also be used to modify imidazolyl, thioether, phenol and amino groups as described by Gurd, F. R. N. in *Methods Enzymol.* (1967) 11, 532. N-Maleimide derivatives are also considered selective towards sulfhydryl groups, but may additionaly be useful in coupling to amino groups under certain conditions. Reagents such as 2-iminothiolane, e.g. as described by Traut, R. et al. in *Biochemistry* (1973) 12, 3266, which introduce a thiol group through conversion of an amino group, may be considered as sulfhydryl reagents if linking occurs through the formation of disulphide bridges. Thus reagents which introduce reactive disulphide bonds into either the reporter or the vector may be useful, since linking may be brought about by disulphide exchange between the vector and reporter; examples of such reagents include Ellman=s reagent (DTNB), 4,4'-dithiodipyridine, methyl-3-nitro-2-pyridyl disulphide and methyl-2-pyridyl disulphide (described by Kimura, T. et al. in *Analyt. Biochem.* (1982) 122, 271).

Examples of reactive moieties capable of reaction with amino groups include alkylating and acylating agents. Representative alkylating agents include:

i) α-haloacetyl compounds, which show specificity towards amino groups in the absence of reactive thiol groups and are of the type X—CH$_2$CO— (where X=Cl, Br or I), e.g. as described by Wong, Y-H. H. in *Biochemistry* (1979) 24, 5337;

ii) N-maleimide derivatives, which may react with amino groups either through a Michael type reaction or through acylation by addition to the ring carbonyl group as described by Smyth, D. G. et al. in *J. Am. Chem. Soc.* (1960) 82, 4600 and *Biochem. J.* (1964) 91, 589;

iii) aryl halides such as reactive nitrohaloaromatic compounds;

iv) alkyl halides as described by McKenzie, J. A. et al. in *J. Protein Chem.* (1988) 7, 581;

v) aldehydes and ketones capable of Schiff's base formation with amino groups, the adducts formed usually being stabilised through reduction to give a stable amine;

vi) epoxide derivatives such as epichlorohydrin and bisoxiranes, which may react with amino, sulfhydryl or phenolic hydroxyl groups;

vii) chlorine-containing derivatives of s-triazines, which are very reactive towards nucleophiles such as amino, sufhydryl and hydroxy groups;

viii) aziridines based on s-triazine compounds detailed above, e.g. as described by Ross, W. C. J. in *Adv. Cancer Res.* (1954) 2, 1, which react with nucleophiles such as amino groups by ring opening;

ix) squaric acid diethyl esters as described by Tietze, L. F. in *Chem. Ber.* (1991) 124, 1215; and x) α-haloalkyl ethers, which are more reactive alkylating agents than normal alkyl halides because of the activation caused by the ether oxygen atom, e.g. as described by Benneche, T. et al. in *Eur. J. Med. Chem.* (1993) 28, 463.

Representative amino-reactive acylating agents include:

i) isocyanates and isothiocyanates, particularly aromatic derivatives, which form stable urea and thiourea derivatives respectively and have been used for protein crosslinking as described by Schick, A. F. et al. in *J. Biol. Chem.* (1961) 236, 2477;

ii) sulfonyl chlorides, which have been described by Herzig, D. J. et al. in *Biopolymers* (1964) 2, 349 and which may be useful for the introduction of a fluorescent reporter group into the linker;

iii) Acid halides;

iv) Active esters such as nitrophenylesters or N-hydroxysuccinimidyl esters;

v) acid anhydrides such as mixed, symmetrical or N-carboxyanhydrides;

vi) other useful reagents for amide bond formation as described by Bodansky, M. et al. in >*Principles of Peptide Synthesis*= (1984) Springer-Verlag;

vii) acylazides, e.g. wherein the azide group is generated from a preformed hydrazide derivative using sodium nitrite, e.g. as described by Wetz, K. et al. in *Anal. Biochem.* (1974) 58, 347;

viii) azlactones attached to polymers such as bis-acrylamide, e.g. as described by Rasmussen, J. K. in *Reactive Polymers* (1991) 16, 199; and ix) Imidoesters, which form stable amidines on reaction with amino groups, e.g. as described by Hunter, M. J. and Ludwig, M. L. in *J. Am. Chem. Soc.* (1962) 84, 3491.

Carbonyl groups such as aldehyde functions may be reacted with weak protein bases at a pH such that nucleophilic protein side-chain functions are protonated. Weak bases include 1,2-aminothiols such as those found in N-terminal cysteine residues, which selectively form stable 5-membered thiazolidine rings with aldehyde groups, e.g. as described by Ratner, S. et al. in *J. Am. Chem. Soc.* (1937) 59, 200. Other weak bases such as phenyl hydrazones may be used, e.g. as described by Heitzman, H. et al. in *Proc. Natl. Acad. Sci. USA* (1974) 71, 3537.

Aldehydes and ketones may also be reacted with amines to form Schiff's bases, which may advantageously be stabilised through reductive amination. Alkoxylamino moieties readily react with ketones and aldehydes to produce stable alkoxamines, e.g. as described by Webb, R. et al. in *Bioconjugate Chem.* (1990) 1, 96.

Examples of reactive moieties capable of reaction with carboxyl groups include diazo compounds such as diazoacetate esters and diazoacetamides, which react with high specificity to generate ester groups, e.g. as described by Herriot R. M. in *Adv. Protein Chem.* (1947) 3, 169. Carboxylic acid modifying reagents such as carbodiimides, which react through O-acylurea formation followed by amide bond formation, may also usefully be employed; linking may be facilitated through addition of an amine or may result in direct vector-receptor coupling. Useful water soluble carbodiimides include 1-cyclohexyl-3-(2-morpholinyl-4-ethyl)carbodiimide (CMC) and 1-ethyl-3-(3-dimethylaminopropyl)carbodiimide (EDC), e.g. as described by Zot, H. G. and Puett, D. in *J. Biol. Chem.* (1989) 264, 15552. Other useful carboxylic acid modifying reagents include isoxazolium derivatives such as Woodwards reagent K; chloroformates such as p-nitrophenylchloroformate; carbonyldiimidazoles such as 1,1'-carbonyldiimidazole; and N-carbalkoxydihydroquinolines such as N-(ethoxycarbonyl)-2-ethoxy-1,2-dihydroquinoline.

Other potentially useful reactive moieties include vicinal diones such as p-phenylenediglyoxal, which may be used to react with guanidinyl groups, e.g. as described by Wagner et al. in *Nucleic acid Res.* (1978) 5, 4065; and diazonium salts, which may undergo electrophilic substitution reactions, e.g. as described by Ishizaka, K. and Ishizaka T. in *J. Immunol.* (1960) 85, 163. Bis-diazonium compounds are readily prepared by treatment of aryl diamines with sodium nitrite in acidic solutions. It will be appreciated that functional groups in the reporter and/or vector may if desired be converted to other functional groups prior to reaction, e.g. to confer additional reactivity or selectivity. Examples of methods useful for this purpose include conversion of amines to carboxylic acids using reagents such as dicarboxylic anhydrides; conversion of amines to thiols using reagents such as N-acetylhomocysteine thiolactone, S-acetylmercaptosuccinic anhydride, 2-iminothiolane or thiol-containing succinimidyl derivatives; conversion of thiols to carboxylic acids using reagents such as α-haloacetates; conversion of thiols to amines using reagents such as ethylenimine or 2-bromoethylamine; conversion of carboxylic acids to amines using reagents such as carbodiimides followed by diamines; and conversion of alcohols to thiols using reagents such as tosyl chloride followed by transesterification with thioacetate and hydrolysis to the thiol with sodium acetate.

Vector-reporter coupling may also be effected using enzymes as zero-length crosslinking agents; thus, for example, transglutaminase, peroxidase and xanthine oxidase have been used to produce crosslinked products.

Reverse proteolysis may also be used for crosslinking through amide bond formation.

Non-covalent vector-reporter coupling may, for example, be effected by electrostatic charge interactions e.g. between a polylysinyl-functionalised reporter and a polyglutamyl-functionalised vector, through chelation in the form of stable metal complexes or through high affinity binding interaction such as avidin/biotin binding.

A vector which comprises or is coupled to a peptide, lipo-oligosaccharide or lipopeptide linker which contains a element capable of mediating membrane insertion may also be useful. One example is described by Leenhouts, J. M. et al. in *Febs Letters* (1995) 370(3), 189–192.

Coupling may also be effected using avidin or streptavidin, which have four high affinity binding sites for biotin. Avidin may therefore be used to conjugate vector to reporter if both vector and reporter are biotinylated. Examples are described by Bayer, E. A. and Wilchek, M. in *Methods Biochem. Anal.* (1980) 26, 1. This method may also be extended to include linking of reporter to reporter, a process which may encourage association of the agent and consequent potentially increased efficacy. Alternatively, avidin or streptavidin may be attached directly to the surface of reporter particles.

Non-covalent coupling may also utilise the bifunctional nature of bispecific immunoglobulins. These molecules can specifically bind two antigens, thus linking them. For example, either bispecific IgG or chemically engineered bispecific F(ab)=$_2$ fragments may be used as linking agents. Heterobifunctional bispecific antibodies have also been reported for linking two different antigens, e.g. as described by Bode, C. et al. in *J. Biol. Chem.* (1989) 264, 944 and by Staerz, U. D. et al. in *Proc. Natl. Acad. Sci. USA* (1986) 83, 1453. Similarly, any reporter and/or vector containing two or more antigenic determinants (e.g. as described by Chen, Aa et al. in *Am. J. Pathol.* (1988) 130, 216) may be crosslinked by antibody molecules and lead to formation of cross-linked assemblies of agents of formula I of potentially increased efficacy.

So-called zero-length linking agents, which induce direct covalent joining of two reactive chemical groups without introducing additional linking material (e.g. as in amide bond formation induced using carbodiimides or enzymatically) may, if desired, be used in accordance with the invention, as may agents such as biotin/avidin systems which induce non-covalent reporter-vector linking and agents which induce electrostatic interactions.

Most commonly, however, the linking agent will comprise two or more reactive moieties, e.g. as described above, connected by a spacer element. The presence of such a spacer permits bifunctional linkers to react with specific functional groups within a molecule or between two different molecules, resulting in a bond between these two components and introducing extrinsic linker-derived material into the reporter-vector conjugate. The reactive moieties in a linking agent may be the same (homobifunctional agents) or different (heterobifunctional agents or, where several dissimilar reactive moieties are present, heteromultifunctional agents), providing a diversity of potential reagents that may bring about covalent bonding between any chemical species, either intramolecularly or intermolecularly.

The nature of extrinsic material introduced by the linking agent may have a critical bearing on the targeting ability and general stability of the ultimate product. Thus it may be desirable to introduce labile linkages, e.g. containing spacer arms which are biodegradable or chemically sensitive or which incorporate enzymatic cleavage sites. Alternatively the spacer may include polymeric components, e.g. to act as surfactants and enhance the stability of the agent. The spacer may also contain reactive moieties, e.g. as described above to enhance surface crosslinking.

Spacer elements may typically consist of aliphatic chains which effectively separate the reactive moieties of the linker by distances of between 5 and 30 Å. They may also comprise macromolecular structures such as poly(ethylene glycols). Such polymeric structures, hereinafter referred to as PEGs, are simple, neutral polyethers which have been given much attention in biotechnical and biomedical applications (see e.g. Milton Harris, J. (ed) "*Poly(ethylene glycol) chemistry, biotechnical and biomedical applications*" Plenum Press, New York, 1992). PEGs are soluble in most solvents, including water, and are highly hydrated in aqueous environments, with two or three water molecules bound to each ethylene glycol segment; this has the effect of preventing adsorption either of other polymers or of proteins onto PEG-modified surfaces. PEGs are known to be nontoxic and not to harm active proteins or cells, whilst covalently linked PEGs are known to be non-immunogenic and non-antigenic. Furthermore, PEGs may readily be modified and bound to other molecules with only little effect on their chemistry. Their advantageous solubility and biological properties are apparent from the many possible uses of PEGs and copolymers thereof, including block copolymers such as PEG-polyurethanes and PEG-polypropylenes.

Appropriate molecular weights for PEG spacers used in accordance with the invention may, for example, be between 120 Daltons and 20 kDaltons.

The major mechanism for uptake of particles by the cells of the reticuloendothelial system (RES) is opsonisation by plasma proteins in blood; these mark foreign particles which are then taken up by the RES. The biological properties of PEG spacer elements used in accordance with the invention may serve to increase the circulation time of the agent in a similar manner to that observed for PEGylated liposomes (see e.g. Klibanov, A. L. et al. in *FEBS Letters* (1990) 268, 235–237 and Blume, G. and Cevc, G. in *Biochim. Biophys. Acta* (1990) 1029, 91–97). Increased coupling efficiency to areas of interest may also be achieved using antibodies bound to the terminii of PEG spacers (see e.g. Maruyama, K.

et al. in *Biochim. Biophys. Acta* (1995) 1234, 74–80 and Hansen, C. B. et al. in *Biochim. Biophys. Acta* (1995) 1239, 133–144).

Other representative spacer elements include structural-type polysaccharides such as polygalacturonic acid, glycosaminoglycans, heparinoids, cellulose and marine polysaccharides such as alginates, chitosans and carrageenans; storage-type polysaccharides such as starch, glycogen, dextran and aminodextrans; polyamino acids and methyl and ethyl esters thereof, as in homo- and co-polymers of lysine, glutamic acid and aspartic acid; and polypeptides, oligosaccharides and oligonucleotides, which may or may not contain enzyme cleavage sites.

In general, spacer elements may contain cleavable groups such as vicinal glycol, azo, sulfone, ester, thioester or disulphide groups. Spacers containing biodegradable methylene diester or diamide groups of formula

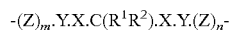

[where X and Z are selected from —O—, —S—, and —NR— (where R is hydrogen or an organic group); each Y is a carbonyl, thiocarbonyl, sulphonyl, phosphoryl or similar acid-forming group: m and n are each zero or 1; and $R^1$ and $R^2$ are each hydrogen, an organic group or a group —X.Y.$(Z)_m$-, or together form a divalent organic group] may also be useful; as discussed in, for example, WO-A-9217436 such groups are readily biodegraded in the presence of esterases, e.g. in vivo, but are stable in the absence of such enzymes. They may therefore advantageously be linked to therapeutic agents to permit slow release thereof.

Poly[N-(2-hydroxyethyl)methacrylamides] are potentially useful spacer materials by virtue of their low degree of interaction with cells and tissues (see e.g. Volfová, I., Ríhová, B. and V. R. and Vetvicka, P. in *J. Bioact. Comp. Polymers* (1992) 7, 175–190). Work on a similar polymer consisting mainly of the closely related 2-hydroxypropyl derivative showed that it was endocytosed by the mononuclear phagocyte system only to a rather low extent (see Goddard, P., Williamson, I., Bron, J., Hutchkinson, L. E., Nicholls, J. and Petrak, K. in *J. Bioct. Compat. Polym.* (1991) 6, 4–24.).

Other potentially useful poymeric spacer materials include:

i) copolymers of methyl methacrylate with methacrylic acid; these may be erodible (see Lee, P. I. in *Pharm. Res.* (1993) 10, 980) and the carboxylate substituents may cause a higher degree of swelling than with neutral polymers;

ii) block copolymers of polymethacrylates with biodegradable polyesters (see e.g. San Roman, J. and Guillen-Garcia, P. in *Biomaterials* (1991) 12, 236–241);

iii) cyanoacrylates, i.e. polymers of esters of 2-cyanoacrylic acid—these are biodegradable and have been used in the form of nanoparticles for selective drug delivery (see Forestier, F., Gerrier, P., Chaumard, C., Quero, A. M., Couvreur, P. and Labarre, C. in *J. Antimicrob. Chemoter.* (1992) 30, 173–179);

iv) polyvinyl alcohols, which are water-soluble and generally regarded as biocompatible (see e.g. Langer, R. in *J. Control. Release* (1991) 16, 53–60);

v) copolymers of vinyl methyl ether with maleic anhydride, which have been stated to be bioerodible (see Finne, U., Hannus, M. and Urtti, A. in *Int. J. Pharm.* (1992) 78. 237–241);

vi) polyvinylpyrrolidones, e.g. with molecular weight less than about 25,000, which are rapidly filtered by the kidneys (see Hespe, W., Meier, A. M. and Blankwater, Y. M. in *Arzeim.-Forsch./Drug Res.* (1977) 27, 1158–1162);

vii) polymers and copolymers of short-chain aliphatic hydroxyacids such as glycolic, lactic, butyric, valeric and caproic acids (see e.g. Carli, F. in *Chim. Ind. (Milan)* (1993) 75, 494–9), including copolymers which incorporate aromatic hydroxyacids in order to increase their degradation rate (see Imasaki, K., Yoshida, M., Fukuzaki, H., Asano, M., Kumakura, M., Mashimo, T., Yamanaka, H. and Nagai. T. in *Int. J. Pharm.* (1992) 81, 31–38);

viii) polyesters consisting of alternating units of ethylene glycol and terephthalic acid, e.g. Dacron$^R$, which are non-degradable but highly biocompatible;

ix) block copolymers comprising biodegradable segments of aliphatic hydroxyacid polymers (see e.g. Younes, H., Nataf, P. R., Cohn, D., Appelbaum, Y. J., Pizov, G. and Uretzky, G. in *Biomater. Artif. Cells Artif. Organs* (1988) 16, 705–719), for instance in conjunction with polyurethanes (see Kobayashi, H., Hyon, S. H. and Ikada, Y. in "Water-curable and biodegradable prepolymers"—*J. Biomed. Mater. Res.* (1991) 25, 1481–1494);

x) polyurethanes, which are known to be well-tolerated in implants, and which may be combined with flexible Asoft≡segments, e.g. comprising poly(tetra methylene glycol), poly(propylene glycol) or poly(ethylene glycol)) and aromatic Ahard≡segments, e.g. comprising 4,4'-methylenebis(phenylene isocyanate) (see e.g. Ratner, B. D., Johnston, A. B. and Lenk, T. J. in *J. Biomed. Mater. Res.: Applied Biomaterials* (1987) 21, 59–90; Sa Da Costa, V. et al. in *J. Coll. Interface Sci.* (1981) 80, 445–452 and Affrossman, S. et al. in *Clinical Materials* (1991) 8, 25–31);

xi) poly(1,4-dioxan-2-ones), which may be regarded as biodegradable esters in view of their hydrolysable ester linkages (see e.g. Song, C. X., Cui, X. M. and Schindler, A. in *Med. Biol. Eng. Comput.* (1993) 31, S147–150), and which may include glycolide units to improve their absorbability (see Bezwada, R. S., Shalaby, S. W. and Newman, H. D. J. in *Agricultural and synthetic polymers: Biodegradability and utilization* (1990) (ed Glass, J. E. and Swift, G.), 167–174—ACS symposium Series, #433, Washington D.C., U.S.A.—American Chemical Society);

xii) polyanhydrides such as copolymers of sebacic acid (octanedioic acid) with bis(4-carboxy-phenoxy)propane, which have been shown in rabbit studies (see Brem, H., Kader, A., Epstein, J. I., Tamargo, R. J., Domb, A., Langer, R. and Leong, K. W. in *Sel. Cancer Ther.* (1989) 5, 55–65) and rat studies (see Tamargo, R. J., Epstein, J. I., Reinhard, C. S., Chasin, M. and Brem, H. in *J. Biomed. Mater. Res.* (1989) 23, 253–266) to be useful for controlled release of drugs in the brain without evident toxic effects;

xiii) biodegradable polymers containing ortho-ester groups, which have been employed for controlled release in vivo (see Maa, Y. F. and Heller, J. in *J. Control. Release* (1990) 14, 21–28); and xiv) polyphosphazenes, which are inorganic polymers consisting of alternate phosphorus and nitrogen atoms (see Crommen, J. H., Vandorpe, J. and Schacht, E. H. in *J. Control. Release* (1993) 24, 167–180).

The following tables list linking agents which may be useful in targetable agents in accordance with the invention.

Heterobifunctional Linking Agents

| Linking agent | Reactivity 1 | Reactivity 2 | Comments |
|---|---|---|---|
| ABH | carbohydrate | photoreactive | |
| ANB-NOS | —NH$_2$ | photoreactive | |
| APDP(1) | —SH | photoreactive | iodinable disulphide linker |
| APG | —NH$_2$ | photoreactive | reacts selectively with Arg at pH 7–8 |
| ASIB(1) | —SH | photoreactive | iodinable |
| ASBA(1) | —COOH | photoreactive | iodinable |
| EDC | —NH$_2$ | —COOH | zero-length linker |
| GMBS | —NH$_2$ | —SH | |
| sulfo-GMBS | —NH$_2$ | —SH | water-soluble |
| HSAB | —NH$_2$ | photoreactive | |
| sulfo-HSAB | —NH$_2$ | photoreactive | water-soluble |
| MBS | —NH$_2$ | —SH | |
| sulfo-MBS | —NH$_2$ | —SH | water-soluble |
| M$_2$C$_2$H | carbohydrate | —SH | |
| MPBH | carbohydrate | —SH | |
| NHS-ASA(1) | —NH$_2$ | photoreactive | iodinable |
| sulfo-NHS-ASA(1) | —NH$_2$ | photoreactive | water-soluble, iodinable |
| sulfo-NHS-LC-ASA(1) | —NH$_2$ | photoreactive | water-soluble, iodinable |
| PDPH | carbohydrate | —SH | disulphide linker |
| PNP-DTP | —NH$_2$ | photoreactive | |
| SADP | —NH$_2$ | photoreactive | disulphide linker |
| sulfo-SADP | —NH$_2$ | photoreactive | water-soluble disulphide linker |
| SAED | —NH$_2$ | photoreactive | disulphide linker |
| SAND | —NH$_2$ | photoreactive | water-soluble disulphide linker |
| SANPAH | —NH$_2$ | photoreactive | |
| sulfo-SANPAH | —NH$_2$ | photoreactive | water-soluble |
| SASD(1) | —NH$_2$ | photoreactive | water-soluble iodinable disulphide linker |
| SIAB | —NH$_2$ | —SH | |
| sulfo-SIAB | —NH$_2$ | —SH | water-soluble |
| SMCC | —NH$_2$ | —SH | |
| sulfo-SMCC | —NH$_2$ | —SH | water-soluble |
| SMPB | —NH$_2$ | —SH | |
| sulfo-SMPB | —NH$_2$ | —SH | water-soluble |
| SMPT | —NH$_2$ | —SH | |
| sulfo-LC-SMPT | —NH$_2$ | —SH | water-soluble |
| SPDP | —NH$_2$ | —SH | |
| sulfo-SPDP | —NH$_2$ | —SH | water-soluble |
| sulfo-LC-SPDP | —NH$_2$ | —SH | water-soluble |
| sulfo-SAMCA (2) | —NH$_2$ | photoreactive | |
| sulfo-SAPB | —NH$_2$ | photoreactive | water-soluble |

Notes:
(1) = iodinable;
(2) = fluorescent

Homobifunctional Linking Agents

| Linking agent | Reactivity | Comments |
|---|---|---|
| BS | —NH$_2$ | |
| BMH | —SH | |
| BASED (1) | photoreactive | iodinable disulphide linker |
| BSCOES | —NH$_2$ | |
| sulfo-BSCOES | —NH$_2$ | water-soluble |
| DFDNB | —NH$_2$ | |
| DMA | —NH$_2$ | |
| DMP | —NH$_2$ | |
| DMS | —NH$_2$ | |
| DPDPB | —SH | disulphide linker |
| DSG | —NH$_2$ | |
| DSP | —NH$_2$ | disulphide linker |
| DSS | —NH$_2$ | |
| DST | —NH$_2$ | |
| sulfo-DST | —NH$_2$ | water-soluble |
| DTBP | —NH$_2$ | disulphide linker |
| DTSSP | —NH$_2$ | disulphide linker |
| EGS | —NH$_2$ | |
| sulfo-EGS | —NH$_2$ | water-soluble |
| SPBP | —NH$_2$ | |

Biotinylation Agents

| Agent | Reactivity | Comments |
|---|---|---|
| biotin-BMCC | —SH | |
| biotin-DPPE* | | preparation of biotinylated liposomes |
| biotin-LC-DPPE* | | preparation of biotinylated liposomes |
| biotin-HPDP | —SH | disulphide linker |
| biotin-hydrazide | carbohydrate | |
| biotin-LC-hydrazide | carbohydrate | |
| iodoacetyl-LC-biotin | —NH$_2$ | |
| NHS-iminobiotin | —NH$_2$ | reduced affinity for avidin |
| NHS-SS-biotin | —NH$_2$ | disulphide linker |
| photoactivatable biotin | nucleic acids | |
| sulfo-NHS-biotin | —NH$_2$ | water-soluble |
| sulfo-NHS-LC-biotin | —NH$_2$ | |

Notes:
DPPE = dipalmitoylphosphatidylethanolamine;
LC = long chain

Agents for Protein Modification

| Agent | Reactivity | Function |
|---|---|---|
| Ellman's reagent | —SH | quantifies/detects/protects |
| DTT | —S.S— | reduction |
| 2-mercaptoethanol | —S.S— | reduction |
| 2-mercaptylamine | —S.S— | reduction |
| Traut's reagent | —NH$_2$ | introduces —SH |
| SATA | —NH$_2$ | introduces protected —SH |
| AMCA-NHS | —NH$_2$ | fluorescent labelling |
| AMCA-hydrazide | carbohydrate | fluorescent labelling |
| AMCA-HPDP | —S.S— | fluorescent labelling |
| SBF-chloride | —S.S— | fluorescent detection of —SH |
| N-ethylmaleimide | —S.S— | blocks —SH |
| NHS-acetate | —NH$_2$ | blocks and acetylates —NH$_2$ |
| citraconic anhydride | —NH$_2$ | reversibly blocks and introduces negative charges |
| DTPA | —NH$_2$ | introduces chelator |
| BNPS-skatole | tryptophan | cleaves tryptophan residue |
| Bolton-Hunter | —NH$_2$ | introduces iodinable group |

In addition to the already contemplated straight chain and branched PEG-like linkers (e.g. polyethylene glycols and other containing 2 to 100 recurring units of ethylene oxide), linkers in the VLR system can be independently a chemical bond or the residue of a linking group. The phrase "residue of a linking group" as used herein refers to a moiety that remains, results, or is derived from the reaction of a vector reactive group with a reactive site on a vector. The phrase "vector reactive group" as used herein refers to any group which can react with functional groups typically found on vectors, the dervivitization of which only minimally effects the ability of the vector to bind to its receptor. However, it is specifically contemplated that such vector reactive groups can also react with functional groups typically found on relevant protein molecules. Thus, in one aspect the linkers useful in the practice of this invention derive from those groups which can react with any relevant molecule which comprises a vector as described above containing a reactive group, whether or not such relevant molecule is a protein, to form a linking group.

Preferred linking groups are derived from vector reactive groups selected from but not limited to:

a group that will react directly with carboxy, aldehyde, amine (NHR), alcohols, sulfhydryl groups, activated methylenes and the like, on the vector, for example, active halogen containing groups including, for example, chloromethylphenyl groups and chloroacetyl [$ClCH_2C(=O)$—] groups, activated 2-(leaving group substituted)-ethylsulfonyl and ethylcarbonyl groups such as 2-chloroethylsulfonyl and 2-chloroethylcarbonyl; vinylsulfonyl; vinylcarbonyl; epoxy; isocyanato; isothiocyanato; aldehyde; aziridine; succinimidoxycarbonyl; activated acyl groups such as carboxylic acid halides; mixed anhydrides and the like.

A group that can react readily with modified vector molecules containing a vector reactive group, i.e., vectors containing a reactive group modified to contain reactive groups such as those mentioned in (1) above, for example, by oxidation of the vector to an aldehyde or a carboxylic acid, in which case the "linking group" can be derived from reactive groups selected from amino, alkylamino, arylamino, hydrazino, alkylhydrazino, arylhydrazino, carbazido, semicarbazido, thiocarbazido, thiosemicarbazido, sulfhydryl, sulfhydrylalkyl, sulfhydrylaryl, hydroxy, carboxy, carboxyalkyl and carboxyaryl. The alkyl portions of said linking groups can contain from 1 to about 20 carbon atoms. The aryl portions of said linking groups can contain from about 6 to about 20 carbon atoms; and a group that can be linked to the vector containing a reactive group, or to the modified vector as noted in (1) and (2) above by use of a crosslinking agent. The residues of certain useful crosslinking agents, such as, for example, homobifunctional and heterobifunctional gelatin hardeners, bisepoxides, and bisisocyanates can become a part of a linking group during the crosslinking reaction. Other useful crosslinking agents, however, can facilitate the crosslinking, for example, as consumable catalysts, and are not present in the final conjugate. Examples of such crosslinking agents are carbodiimide and carbamoylonium crosslinking agents as disclosed in U.S. Pat. No. 4,421,847 and the ethers of U.S. Pat. No. 4,877,724. With these crosslinking agents, one of the reactants such as the vector must have a carboxyl group and the other such as a long chain spacer must have a reactive amine, alcohol, or sulfhydryl group. In amide bond formation, the crosslinking agent first reacts selectively with the carboxyl group, then is split out during reaction of the thus "activated" carboxyl group with an amine to form an amide linkage between thus covalently bonding the two moieties. An advantage of this approach is that crosslinking of like molecules, e.g., vector to vector is avoided, whereas the reaction of, for example, homobifunctional crosslinking agents is nonselective and unwanted crosslinked molecules are obtained.

Preferred useful linking groups are derived from various heterobifunctional cross-linking reagents such as those listed in the Pierce Chemical Company Immunotechnology Catalog—Protein Modification Section, (1995 and 1996). Useful non-limiting examples of such reagents include:
Sulfo-SMCC Sulfosuccinimidyl 4-(N-maleimidomethyl)cyclohexane-1-carboxylate.
Sulfo-SIAB Sulfosuccinimidyl (4-iodoacetyl)aminobenzoate.
Sulfo-SMPB Sulfosuccinimidyl 4-(p-maleimidophenyl)butyrate.
2-IT 2-Iminothiolane.
SATA N-Succinimidyl S-acetylthioacetate.

In addition to the foregoing description, the linking groups, in whole or in part, can also be comprised of and derived from complementary sequences of nucleotides and residues of nucleotides, both naturally occurring and modified, preferably non-self-associating oligonucleotide sequences. Particularly useful, non-limiting reagents for incorporation of modified nucleotide moieties containing reactive functional groups, such as amine and sulfhydryl groups, into an oligonucleotide sequence are commercially available from, for example, Clontech Laboratories Inc. (Palo Alto Calif.) and include Uni-Link AminoModifier (Catalog #5190), Biotin-ON phosphoramidite (Catalog #5191), N-MNT-C6-Amino-Modifier (Catalog #5202), AminoModifier II (Catalog #5203), DMT-C6-3'Amine-ON (Catalog #5222), C6-ThiolModifier (Catalog #5211), and the like. In one aspect, linking groups of this invention are derived from the reaction of a reactive functional group such as an amine or sulfhydryl group as are available in the above Clontech reagents, one or more of which has been incorporated into an oligonucleotide sequence, with, for example, one or more of the previously described vector reactive groups such as a heterobifunctional group on the vector.

By attaching two complementary oligonucleotide sequences one to the vector and the other to the reporter the resulting double-stranded hybridized oligonucleotide then comprises the linking group between the vector and reporter.

Other polymer systems that serve as linkers include:
Poly(L or D or DL-amino acids)=proteins and peptides; naturally occuring or synthetic
Pseudo Poly(amino acids)=(amino acids linked by non-amide bonds)
Poly(L or D or DL-lactide) and the co-polymers e.g Poly-(L-lactide/DL-lactide)Poly(glycolide)
L-lactide/glycolide co-polymers
Poly-,-caprolactone and its co-polymers
Polyanhydrides
Poly(ortho esters)
Polyphosphazenes
Long-chain straight or branched lipids (& phospholipids)
Sugars and carbohydrates
Oligonucleotides (see above)

as well as mixtures of the above.

Linking agents used in accordance with the invention will in general bring about linking of vector to reporter or reporter to reporter with some degree of specificity, and may also be used to attach one or more therapeutically active agents.

The present invention accordingly provides a tool for therapeutic drug delivery in combination with vector-mediated direction of the product to the desired site. By "therapeutic" or "drug" is meant an agent having a beneficial effect on a specific disease in a living human or non-human animal.

Therapeutic compounds used in accordance with the present invention may be encapsulated in the interior of a molecular aggregate or particulate linker or attached to or incorporated in the encapsulating walls of a vesicular linker. Thus, the therapeutic compound may be linked to a part of the surface, for example through covalent or ionic bonds, or may be physically mixed into an encapsulating material, particularly if the drug has similar polarity or solubility to the material, so as to prevent it from leaking out of the product before it is intended to act in the body. The release of the drug may be initiated merely by wetting contact with blood following administration or as a consequence of other internal or external influences, e.g. dissolution processes catalyzed by enzymes or the use of where the linker-reporter is a gas containing vesicle.

The therapeutic substance may be covalently linked to the encapsulating membrane surface of a vesicular linker using a suitable linking agent, e.g. as described herein. Thus, for example, one may initially prepare a phospholipid derivative to which the drug is bonded through a biodegradable bond or linker, and then incorporate this derivative into the material used to prepare the vesicle membrane, as described above. Alternatively, the agent may initially be prepared without the therapeutic, which may then be coupled to or coated onto particulate (eg. vesicular) agents prior to use. Thus, for example, a therapeutic could be added to a suspension of microbubbles in aqueous media and shaken in order to attach or adhere the therapeutic to the microbubbles.

The therapeutic may for example be a drug or prodrug known for use in treating congestive heart failure or other cadiovascular therapy.

By targeting an agent according to the invention containing a prodrug-activating enzyme to areas of pathology one may image targeting of the enzyme, making it possible to visualise when the agent is targeted properly and when the agent has disappeared from non-target areas. In this way one can determine the optimal time for injection of prodrug into individual patients.

Another alternative is to incorporate a prodrug, a prodrug-activating enzyme and a vector in the same particulate linker reporter in such a way that the prodrug will only be activated after some external stimulus. Such a stimulus may, for example, be a bursting of vesicles by external ultrasound, light stimulation of a chromophoric reporter, or magnetic heating of a superparamagnetic reporter after the desired targeting has been achieved.

So-called prodrugs may also be used in agents according to the invention. Thus drugs may be derivatised to alter their physicochemical properties and to adapt agent of the invention; such derivatised drugs may be regarded as prodrugs and are usually inactive until cleavage of the derivatising group regenerates the active form of the drug.

Therapeutics may easily be delivered in accordance with the invention to the heart and vasculature in general, and to the liver, spleen and kidneys and other regions such as the lymph system, body cavities or gastrointestinal system.

By way of example, where the reporter is a chelated metal species (eg. a paramagnetic metal ion or a metal radionuclide), the linker may comprise a chain attached to a metal chelating group, a polymeric chain with a plurality of metal chelating groups pendant from the molecular backbone or incorporated in the molecular backbone, a branched polymer with metal chelating groups at branch termini (eg. a dendrimeric polychelant), etc. What is required of the linker is simply that it bind the vector and reporter moieties together for an adequate period. By adequate period is meant a period sufficient for the contrast agent to exert its desired effects, eg. to enhance contrast in vivo during a diagnostic imaging procedure.

Thus, in certain circumstances, it may be desirable that the linker biodegrade after administration. By selecting an appropriately biodegradable linker it is possible to modify the biodistribution and bioelimination patterns for the vector and/or reporter. Where vector and/or reporter are biologically active or are capable of exerting undesired effects if retained after the imaging procedure is over, it may be desirable to design in linker biodegradability which ensures appropriate bioelimination or metabolic breakdown of the vector and/or reporter moieties. Thus a linker may contain a biodegradable function which on breakdown yields breakdown products with modified biodistribution patterns which result from the release of the reporter from the vector or from fragmentation of a macromolecular structure. By way of example for linkers which carry chelated metal ion reporters it is possible to have the linker incorporate a biodegradable function which on breakdown releases an excretable chelate compound containing the reporter. Accordingly, biodegradable functions may if desired be incorporated within the linker structure, preferably at sites which are (a) branching sites, (b) at or near attachment sites for vectors or reporters, or (c) such that biodegradation yields physiologically tolerable or rapidly excretable fragments.

Examples of suitable biodegradable functions include ester, amide, double ester, phosphoester, ether, thioether, guanidyl, acetal and ketal functions.

As discussed above, the linker group may if desired have built into its molecular backbone groups which affect the biodistribution of the contrast agent or which ensure appropriate spatial conformation for the contrast agent, eg. to allow water access to chelated paramagnetic metal ion reporters. By way of example the linker backbone may consist in part or essentially totally of one or more polyalkylene oxide chains.

Thus the linker may be viewed as being a composite of optionally biodegradable vector binding ($V_b$) and reporter binding ($R_b$) groups joined via linker backbone ($L_b$) groups, which linker backbone groups may carry linker side chain ($L_{sc}$) groups to modify biodistribution etc. and may themselves incorporate biodegradable functions. The $R_b$ and $V_b$ binding groups may be pendant from the linker backbone or may be at linker backbone termini, for example with one $R_b$ or $V_b$ group at one $L_b$ terminus, with $R_b$ or $V_b$ groups linking together two $L_b$ termini or with one $L_b$ terminus carrying two or more $R_b$ or $V_b$ groups. The $L_b$ and $L_{sc}$ groups will conveniently be oligomeric or polymeric structures (eg. polyesters, polyamides, polyethers, polyamines, oligopeptides, polypeptides, oligo and polysaccharides, oligonucleotides, etc.), preferably structures having at least in part a hydrophilic or lipophilic nature, eg. hydrophilic, amphiphilic or lipophilic structures.

The linker may be low, medium or high molecular weight, eg. up to 2MD. Generally higher molecular weight linkers will be preferred if they are to be loaded with a multiplicity of vectors or reporters or if it is necessary to space vector and reporter apart, or if the linker is itself to serve a role in the modification of biodistribution. In general however linkers will be from 100 to 100 000 D, especially 120 D to 20 kD in molecular weight.

Conjugation of linker to vector and linker to reporter may be by any appropriate chemical conjugation technique, eg.

covalent bonding (for example ester or amide formation), metal chelation or other metal coordinative or ionic bonding, again as described above.

Examples of suitable linker systems include the magnifier polychelant structures of U.S. Pat. No. 5,364,613 and WO90/12050, polyaminoacids (eg. polylysine), functionalised PEG, polysaccharides, glycosaminoglycans, dendritic polymers such as described in WO93/06868 and by Tomalia et al. in Angew. Chem. Int. Ed. Engl. 29:138–175 (1990), PEG-chelant polymers such as described in W94/08629, WO94/09056 and WO96/26754, etc.

Where the reporter is a chelated metal ion, the linker group will generally incorporate the chelant moiety. Alternatively, the chelated metal may be carried on or in a particulate reporter. In either case, conventional metal chelating groups such as are well known in the fields of radiopharmaceuticals and MRI contrast media may be used, eg. linear, cyclic and branched polyamino-polycarboxylic acids and phosphorus oxyacid equivalents, and other sulphur and/or nitrogen ligands known in the art, eg. DTPA, DTPA-BMA, EDTA, DO3A, TMT (see for example U.S. Pat. No. 5,367,080), BAT and analogs (see for example Ohmono et al., J. Med. Chem. 35: 157–162 (1992) and Kung et al. J. Nucl. Med. 25: 326–332 (1984)), the $N_2S_2$ chelant ECD of Neurolite, MAG (see Jurisson et al. Chem. Rev. 93: 1137–1156 (1993)), HIDA, DOXA (1-oxa-4,7,10-triazacyclododecanetriacetic acid), NOTA (1,4,7-triazacyclononanetriacetic acid), TETA (1,4,8,11-tetraazacyclotetradecanetetraacetic acid), THT 4'-(3-amino-4-methoxy-phenyl)-6,6''-bis(N',N'-dicarboxymethyl-N-methylhydrazino)-2,2':6',2''-terpyridine), etc. In this regard, the reader is referred to the patent literature of Sterling Winthrop, Nycomed (including Nycomed Imaging and Nycomed Salutar), Schering, Mallinckrodt, Bracco and Squibb relating to chelating agents for diagnostic metals, eg. in MR, X-ray and radio-diagnostic agents. See for example U.S. Pat. No. 4,647,447, EP-A-71564, U.S. Pat. No. 4,687,659, WO89/00557, U.S. Pat. No. 4,885,363, and EP-A-232751.

Reporters

The reporter moieties in the contrast agents of the invention may be any moiety capable of detection either directly or indirectly in an in vivo diagnostic imaging procedure, eg. moieties which emit or may be caused to emit detectable radiation (eg. by radioactive decay, fluorescence excitation, spin resonance excitation, etc.), moieties which affect local electromagnetic fields (eg. paramagnetic, superparamagnetic, ferrimagnetic or ferromagnetic species), moieties which absorb or scatter radiation energy (eg. chromophores, particles (including gas or liquid containing vesicles), heavy elements and compounds thereof, etc.), and moieties which generate a detectable substance (eg. gas microbubble generators), etc.

A very wide range of materials detectable by diagnostic imaging modalities is known from the art and the reporter will be selected according to the imaging modality to be used. Thus for example for ultrasound imaging an echogenic material, or a material capable of generating an echogenic material will normally be selected, for X-ray imaging the reporter will generally be or contain a heavy atom (eg. of atomic weight 38 or above), for MR imaging the reporter will either be a non zero nuclear spin isotope (such as $^{19}F$) or a material having unpaired electron spins and hence paramagnetic, superparamagnetic, ferrimagnetic or ferromagnetic properties, for light imaging the reporter will be a light scatterer (eg. a coloured or uncoloured particle), a light absorber or a light emitter, for magnetometric imaging the reporter will have detectable magnetic properties, for electrical impedance imaging the reporter will affect electrical iimpedance and for scintigraphy, SPECT, PET etc. the reporter will be a radionuclide.

Examples of suitable reporters are widely known from the diagnostic imaging literature, eg. magnetic iron oxide particles, gas-containing vesicles, chelated paramagnetic metals (such as Gd, Dy, Mn, Fe etc.). See for example U.S. Pat. No. 4,647,447, WO97/25073, U.S. Pat. No. 4,863,715, U.S. Pat. No. 4,770,183, WO96/09840, WO85/02772, WO92/17212, WO97/29783, EP-A-554213, U.S. Pat. No. 5,228,446, WO91/15243, WO93/05818, WO96/23524, WO96/17628, U.S. Pat. No. 5,387,080, WO95/26205, GB9624918.0, etc.

Particularly preferred as reporters are: chelated paramagnetic metal ions such as Gd, Dy, Fe, and Mn, especially when chelated by macrocyclic chelant groups (eg. tetraazacyclododecane chelants such as DOTA, DO3A, HP-DO3A and analogues thereof) or by linker chelant groups such as DTPA, DTPA-BMA, EDTA, DPDP, etc; metal radionuclide such as $^{90}Y$, $^{99m}Tc$, $^{111}In$, $^{47}Sc$, $^{67}Ga$, $^{51}Cr$, $^{177m}Sn$, $^{67}Cu$, $^{167}Tm$, $^{97}Ru$, $^{188}Re$, $^{177}Lu$, $^{199}Au$, $^{203}Pb$ and $^{141}Ce$; superparamagnetic iron oxide crystals; chromophores and fluorophores having absorption and/or emission maxima in the range 300–1400 nm, especially 600 nm to 1200 nm, in particular 650 to 1000 nm; vesicles containing fluorinated gases (ie. containing materials in the gas phase at 37 EC which are fluorine containing, eg. $SF_6$ or perfluorinated $C_{1-6}$ hydrocarbons or other gases and gas precursors listed in WO97/29783); chelated heavy metal cluster ions (eg. W or Mo polyoxoanions or the sulphur or mixed oxygen/sulphur analogs); covalently bonded non-metal atoms which are either high atomic number (eg. iodine) or are radioactive, eg $^{123}I$, $^{131}I$, etc. atoms; iodinated compound containing vesicles; etc.

Stated generally, the reporter may be (1) a chelatable metal or polyatomic metal-containing ion (ie. TcO, etc), where the metal is a high atomic number metal (eg. atomic number greater than 37), a paramagentic species (eg. a transition metal or lanthanide), or a radioactive isotope, (2) a covalently bound non-metal species which is an unpaired electron site (eg. an oxygen or carbon in a persistant free radical), a high atomic number non-metal, or a radioisotope, (3) a polyatomic cluster or crystal containing high atomic number atoms, displaying cooperative magnetic behaviour (eg. superparamagnetism, ferrimagnetism or ferromagnetism) or containing radionuclides, (4) a gas or a gas precursor (ie. a material or mixture of materials which is gaseous at 37 EC), (5) a chromophore (by which term species which are fluorescent or phosphorescent are included), eg. an inorganic or organic structure, particularly a complexed metal ion or an organic group having an extensive delocalized electron system, or (6) a structure or group having electrical impedance varying characteristics, eg. by virtue of an extensive delocalized electron system.

Examples of particular preferred reporter groups are described in more detail below.

Chelated metal reporters: Metal Radionuclides, Paramagnetic metal ions, Fluorescent metal ions, Heavy metal ions and cluster ions Preferred metal radionuclides include $^{90}Y$, $^{99m}Tc$, $^{111}In$, $^{47}Sc$, $^{67}Ga$, $^{51}Cr$, $^{177m}Sn$, $^{67}Cu$, $^{167}Tm$, $^{97}Ru$, $^{188}Re$, $^{177}Lu$, $^{199}Au$, $^{203}Pb$ and $^{141}Ce$.

Preferred paramagnetic metal ions include ions of transition and lanthanide metals (eg. metals having atomic numbers of 6 to 9, 21–29, 42, 43, 44, or 57–71), in particular ions of Cr, V, Mn, Fe, Co, Ni, Cu, La, Ce, Pr, Nd, Pm, Sm, Eu, Gd, Tb, Dy, Ho, Er, Tm, Yb and Lu, especially of Mn, Cr, Fe, Gd and Dy, more especially Gd.

Preferred fluorescent metal ions include lanthanides, in particular La, Ce, Pr, Nd, Pm, Sm, Eu, Gd, Tb, Dy, Ho, Er, Tm, Yb, and Lu. Eu is especially preferred.

Preferred heavy metal-containing reporters may include atoms of Mo, Bi, Si, and W, and in particular may be polyatomic cluster ions (eg. Bi compounds and W and Mo oxides) as described in WO91/14460, WO92/17215, WO96/40287, and WO96/22914.

The metal ions are desirably chelated by chelant groups on the linker moiety or in or on a particle, (eg. a vesicle or a porous or non-porous inorganic or organic solid), in particular linear, macrocyclic, terpyridine and $N_2S_2$ chelants, such as for example DTPA, DTPA-BMA, EDTA, DO3A, TMT. Further examples of suitable chelant groups are disclosed in U.S. Pat. No. 4,647,447, WO89/00557, U.S. Pat. No. 5,367,080, U.S. Pat. No. 5,364,613, etc.

The linker moiety or the particle may contain one or more such chelant groups, if desired metallated by more than one metal species (eg. so as to provide reporters detectable in different imaging modalities).

Particularly where the metal is non-radioactive, it is preferred that a polychelant linker or particulate reporter be used.

A chelant or chelating group as referred to herein may comprise the residue of one or more of a wide variety of chelating agents that can complex a metal ion or a polyatomic ion (eg. TcO).

As is well known, a chelating agent is a compound containing donor atoms that can combine by coordinate bonding with a metal atom to form a cyclic structure called a chelation complex or chelate. This class of compounds is described in the Kirk-Othmer Encyclopedia of Chemical Technology, Vol. 5, 339–368.

The reside of a suitable chelating agent can be selected from polyphosphates, such as sodium tripolyphosphate and hexametaphosphoric acid; aminocarboxylic acids, such as ethylenediaminetetraacetic acid, N-(2-hydroxy)ethylene-diaminetriacetic acid, nitrilotriacetic acid, N,N-di(2-hydroxyethyl)glycine, ethylenebis(hydroxyphenylglycine) and diethylenetriamine pentacetic acid; 1,3-diketones, such as acetylacetone, trifluoroacetylacetone, and thenoyltrifluoroacetone; hydroxycarboxylic acids, such as tartaric acid, citric acid, gluconic acid, and 5-sulfosalicyclic acid; polyamines, such as ethylenediamine, diethylenetriamine, triethylenetetraamine, and triaminotriethylamine; aminoalcohols, such as triethanolamine and N-(2-hydroxyethyl) ethylenediamine; aromatic heterocyclic bases, such as 2,2'-diimidazole, picoline amine, dipicoline amine and 1,10-phenanthroline; phenols, such as salicylaldehyde, disulfopyrocatechol, and chromotropic acid; aminophenols, such as 8-hydroxyquinoline and oximesulfonic acid; oximes, such as dimethylglyoxime and salicylaldoxime; peptides containing proximal chelating functionality such as polycysteine, polyhistidine, polyaspartic acid, polyglutamic acid, or combinations of such amino acids; Schiff bases, such as disalicylaldehyde 1,2-propylenediimine; tetrapyrroles, such as tetraphenylporphin and phthalocyanine; sulfur compounds, such as toluenedithiol, meso-2,3-dimercaptosuccinic acid, dimercaptopropanol, thioglycolic acid, potassium ethyl xanthate, sodium diethyldithiocarbamate, dithizone, diethyl dithiophosphoric acid, and thiourea; synthetic macrocyclic compounds, such as dibenzo[18]crown-6, $(CH_3)_6$-[14]-4,11]-diene-$N_4$, and (2.2.2-cryptate); phosphonic acids, such as nitrilotrimethylene-phosphonic acid, ethylenediaminetetra(methylenephosphonic acid), and hydroxyethylidenediphosphonic acid, or combinations of two or more of the above agents. The residue of a suitable chelating agent preferably comprises a polycarboxylic acid group and preferred examples include: ethylenediamine-N, N,N',N'-tetraacetic acid (EDTA); N,N,N',N'',N''-diethylene-triaminepentaacetic acid (DTPA); 1,4,7,10-tetraazacyclododecane-N,N',N'',N'''-tetraacetic acid (DOTA); 1,4,7,10-tetraazacyclododecane-N,N',N''-triacetic acid (DO3A); 1-oxa-4,7,10-triazacyclododecane-N,N',N''-triacetic acid (OTTA); trans(1,2)-cyclohexanodiethylene-triamine-pentaacetic acid (CDTPA).

Other suitable residues of chelating agents comprise proteins modified for the chelation of metals such as technetium and rhenium as described in U.S. Pat. No. 5,078,985, the disclosure of which is hereby incorporated by reference.

Suitable residues of chelating agents may also derive from N3S and N2S2 containing compounds, as for example, those disclosed in U.S. Pat. Nos. 4,444,690; 4,670,545; 4,673,562; 4,897,255; 4,965,392; 4,980,147; 4,988,496; 5,021,556 and 5,075,099.

Other suitable residues of chelating are described in WO92/08494, the disclosure of which is hereby incorporated by reference.

Preferred chelating groups are selected from the group consisting of 2-amiomethylpyridine, iminoacetic acid, iminodiacetic acid, ethylenediaminetetraacetic acid (EDTA), diethylenetriaminepentaacetic acid (DTPA), 1,4,7,10-tetraazacyclododecane-1,4,7,10-tetraacetic acid (DOTA), carbonyliminodiacetic acid, methyleneiminoacetic acid, methyleneiminodiacetic acid, ethylenethioethyleneiminoacetic acid, ethylenethioethyleneiminodiacetic acid, TMT, a terpyridinyl group, a chelating agent comprising a terpyridyl group and a carboxymethylamino group, or a salt of any of the foregoing acids. Especially preferred chelating groups are DTPA, DTPA-BMA, DPDP, TMT, DOTA and HPDO3A.

Representative chelating groups are also described in U.S. Pat. No. 5,559,214 A, WO 95/26754, WO 94/08624, WO 94/09056, WO 94/29333, WO 94/08624, WO 94/08629 Al, WO 94/13327 Al and WO 94/12216 Al.

Methods for metallating any chelating agents present are within the level of skill in the art. Metals can be incorporated into a chelant moiety by any one of three general methods: direct incorporation, template synthesis and/or transmetallation. Direct incorporation is preferred.

Thus it is desirable that the metal ion be easily complexed to the chelating agent, for example, by merely exposing or mixing an aqueous solution of the chelating agent-containing moiety with a metal salt in an aqueous solution preferably having a pH in the range of about 4 to about 11. The salt can be any salt, but preferably the salt is a water soluble salt of the metal such as a halogen salt, and more preferably such salts are selected so as not to interfere with the binding of the metal ion with the chelating agent. The chelating agent-containing moiety is preferably in aqueous solution at a pH of between about 5 and about 9, more preferably between pH about 6 to about 8. The chelating agent-containing moiety can be mixed with buffer salts such as citrate, acetate, phosphate and borate to produce the optimum pH. Preferably, the buffer salts are selected so as not to interfere with the subsequent binding of the metal ion to the chelating agent.

In diagnostic imaging, the vector-linker-reporter (VLR) construct preferably contains a ratio of metal radionuclide ion to chelating agent that is effective in such diagnostic imaging applications. In preferred embodiments, the mole ratio of metal ion per chelating agent is from about 1:1,000 to about 1:1.

In radiotherapeutic applications, the VLR preferably contains a ratio of metal radionuclide ion to chelating agent that is effective in such therapeutic applications. In preferred embodiments, the mole ratio of metal ion per chelating agent is from about 1:100 to about 1:1. The radionuclide can be selected, for example, from radioisotopes of Sc, Fe, Pb, Ga, Y, Bi, Mn, Cu, Cr, Zn, Ge, Mo, Ru, Sn, Sr, Sm, Lu, Sb, W, Re, Po, Ta and Tl. Preferred radionuclides include $^{44}$Sc, $^{64}$Cu, $^{67}$Cu, $^{212}$Pb, $^{68}$Ga, $^{90}$Y, $^{153}$Sm, $^{212}$Bi, $^{186}$Re and $^{188}$Re. Of these, especially preferred is $^{90}$Y. These radioisotopes can be atomic or preferably ionic.

The following isotopes or isotope pairs can be used for both imaging and therapy without having to change the radiolabeling methodology or chelator: $^{47}$Sc$_{21}$; $^{141}$Ce$_{58}$; $^{188}$Re$_{75}$; $^{177}$Lu$_{71}$; $^{199}$Au$_{79}$; $^{47}$Sc$_{21}$; $^{131}$I$_{53}$; $^{67}$Cu$_{29}$; $^{131}$I$_{53}$ and $^{123}$I$_{53}$; $^{188}$Re$_{75}$ and $^{99m}$Tc$_{43}$; $^{90}$Y$_{39}$ and $^{87}$Y$_{39}$; $^{47}$Sc$_{21}$ and $^{44}$Sc$_{21}$; $^{90}$Y$_{39}$ and $^{123}$I$_{53}$; $^{146}$Sm$_{62}$ and $^{153}$Sm$_{62}$; and $^{90}$Y$_{39}$ and $^{111}$In$_{49}$.

Where the linker moiety contains a single chelant, that chelant may be attached directly to the vector moiety, eg. via one of the metal coordinating groups of the chelant which may form an ester, amide, thioester or thioamide bond with an amine, thiol or hydroxyl group on the vector. Alternatively the vector and chelant may be directly linked via a functionality attached to the chelant backbone, eg. a CH$_2$-phenyl-NCS group attached to a ring carbon of DOTA as proposed by Meares et al. in JACS 110:6266–6267(1988), or indirectly via a homo or hetero-bifunctional linker, eg. a bis amine, bis epoxide, diol, diacid, difunctionalised PEG, etc. In that event, the bifunctional linker will conveniently provide a chain of 1 to 200, preferably 3 to 30 atoms between vector and chelant residue.

Where the linker moiety contains a plurality of chelant groups, the linker preferably is or contains portions of formula

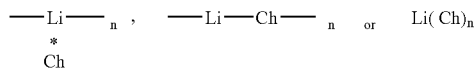

where Ch is a chelant moiety and Li is a linker backbone component, ie. the linker preferably has pendant chelants, in-backbone chelants or terminal chelants or a combination thereof. The pendant and in-backbone polymeric structures may be branched but more preferably are linear and the repeat units (LiCh) or other repeat units in the polymer may have in-backbone or pendant biodistribution modifying groups, eg. polyalkylene groups as in WO94/08629, WO94/09056, and WO96/20754. The terminal chelant structures Li(Ch)$_n$, which may be dendritic polymers as in WO93/06868, may have biodistribution modifying groups attached to termini not occupied by chelants and may have biodegradation enhancing sites within the linker structure as in WO95/28966.

The chelant moieties within the polychelant linker may be attached via backbone functionalization of the chelant or by utilization of one or more of the metal co-ordinating groups of the chelant or by amide or ether bond formation between acid chelant and an amine or hydroxyl carrying linker backbone, eg. as in polylysine-polyDTPA, polylysine-poly-DOTA and in the so-called magnifier polychelants, of WO90/12050. Such polychelant linkers may be conjugated to one or more vector groups either directly (eg. utilizing amine, acid or hydroxyl groups in the polychelant linker) or via a bifunctional linker compound as discussed above for monochelant linkers.

Where the chelated species is carried by a particulate (or molecular aggregate, eg. vesicular) linker, the chelate may for example be an unattached mono or polychelate (such as Gd DTPA-BMA or Gd HP-DO3A) enclosed within the particle or it may be a mono or polychelate conjugated to the particle either by covalent bonding or by interaction of an anchor group (eg. a lipophilic group) on the mono/polychelate with the membrane of a vesicle (see for example WO96/11023).

Non-metal Atomic Reporters

Preferred non-metal atomic reporters include radioisotopes such as $^{123}$I and $^{131}$I as well as non zero nuclear spin atoms such as $^{18}$F, and heavy atoms such as I.

Such reporters, preferably a plurality thereof, eg. 2 to 200, may be covalently bonded to a linker backbone, either directly using conventional chemical synthesis techniques or via a supporting group, eg. a triiodophenyl group.

In an embodiment of this invention, the use of radioisotopes of iodine is specifically contemplated. For example, if the vector or linker is comprised of substituents that can be chemically substituted by iodine in a covalent bond forming reaction, such as, for example, substituents containing hydroxyphenyl functionality, such substituents can be labeled by methods well known in the art with a radioisotope of iodine. The iodine species can be used in therapeutic and diagnostic imaging applications. While, at the same time, a metal in a chelating agent on the same vector-linker can also be used in either therapeutic or diagnostic imaging applications.

As with the metal chelants discussed above, such non-metal atomic reporters may be linked to the linker or carried in or on a particulate linker, eg. in a vesicle (see WO95/26205 and GB9624918.0).

Linkers of the type described above in connection with the metal reporters may be used for non-metal atomic reporters with the non-metal atomic reporter or groups carrying such reporters taking the place of some or all of the chelant groups.

Organic Chromophoric or Fluorophoric Reporters

Preferred organic chromophoric and fluorophoric reporters include groups having an extensive delocalized electron system, eg. cyanines, merocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis (dithiolene) complexes, bis(benzene-dithiolate) complexes, iodoaniline dyes, bis(S,O-dithiolene) complexes, etc. Examples of suitable organic or metallated organic chromophores may be found in "Topics in Applied Chemistry: Infrared absorbing dyes" Ed. M. Matsuoka, Plenum, N.Y. 1990, "Topics in Applied Chemistry: The Chemistry and Application of Dyes", Waring et al., Plenum, N.Y., 1990, "Handbook of Fluorescent Probes and Research Chemicals" Haugland, Molecular Probes Inc, 1996, DE-A-4445065, DE-A-4326466, JP-A-3/228046, Narayanan et al. J. Org. Chem. 60: 2391–2395 (1995), Lipowska et al. Heterocyclic Comm. 1: 427–430 (1995), Fabian et al. Chem. Rev. 92: 1197 (1992), WO96/23525, Strekowska et al. J. Org. Chem. 57: 4578–4580 (1992), WO (Axis) and WO96/17628. Particular examples of chromophores which may be used include xylene cyanole, fluorescein, dansyl, NBD, indocyanine green, DODCI, DTDCI, DOTCI and DDTCI.

Particularly preferred are groups which have absorption maxima between 600 and 1000 nm to avoid interference with haemoglobin absorption (eg. xylene cyanole).

Further such examples include:

cyanine dyes: such as heptamethinecyanine dyes, e.g. compounds 4a to 4g Table II on page 26 of Matsuoka (supra)

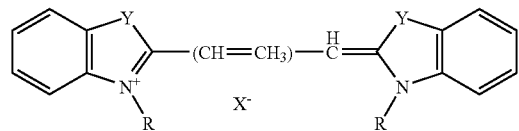

| | | |
|---|---|---|
| 4a: where Y = S, | X = I, | R = Et |
| 4b: where Y = S, | X = ClO$_4$, | R = Et |
| 4c: where Y = Cme$_2$, | X = I, | R = Me |
| 4d: where Y = CMe$_2$, | X = ClO$_4$, | R = Me |
| 4e: where Y = CH=CH, | X = I, | R = Et |
| 4f: where Y = CH=CH, | X = Br, | R = Et |
| 4g: where Y = CH=CH, | X = ClO$_4$, | R = Et | and in Table III on page 28 of Matsuoka (supra), i.e.

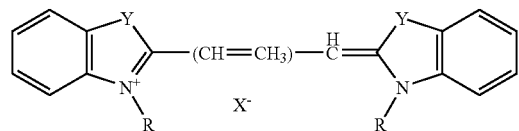

| | | |
|---|---|---|
| where Y = O, | X = I, | R = Me |
| where Y = CMe$_2$, | X = I, | R = Me |
| where Y = S, | X = Br | R = Et; | chalcogenopyrylomethine dyes, e.g., compounds 12 on page 31 of Matsuoka (supra), i.e.

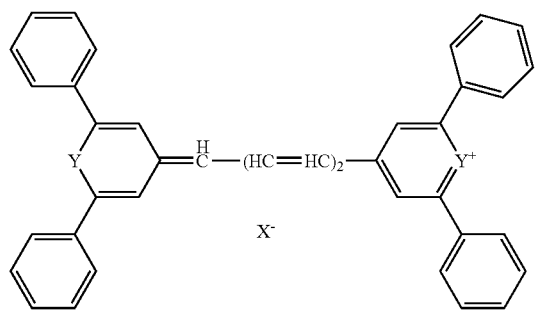

where Y=Te, Se, O or NR;

monochalcogenopyrylomethine dyes, e.g. compounds 13 on page 31, of Matsuoka (supra) i.e.

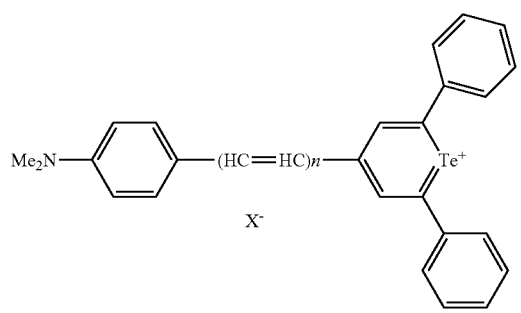

where n=1 or 2;

pyrilium dyes, e.g., compounds 14 (X=O) on page 32 of Matsuoka (supra), i.e.

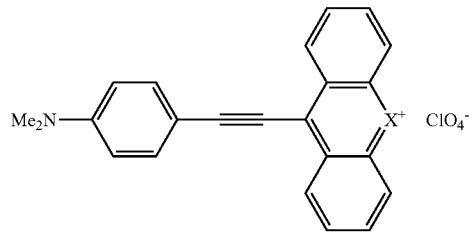

where X=O, S, or Se;

thiapyrilium dyes, e.g. compounds 15 on page 32, and compound I on page 167 of Matsuoka (supra), i.e.

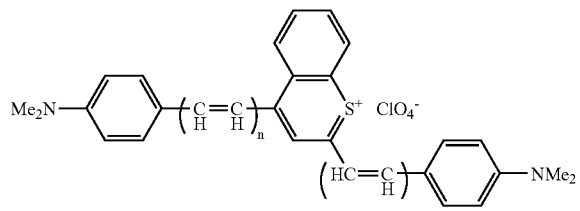

where n=1 or 2;

squarylium dyes, e.g. compound 10 and Table IV on page 30 of Matsuoka (supra), i.e.

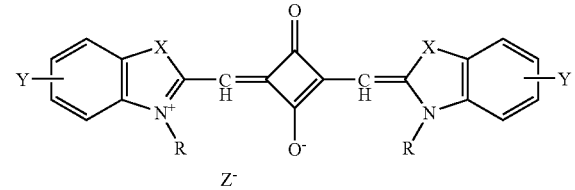

where X=CH=CH, Y=H, and R=Et,
X=S, Y=H, and R=Et, and
X=CMe₂, Y=H, and R=Me,
and compound 6, page 26, of Matsuoka (supra), i.e.

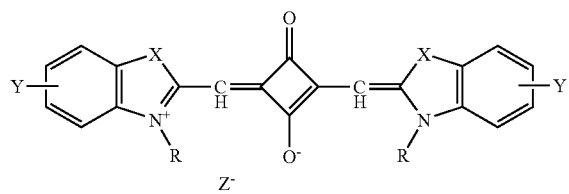

where X=CH=CH, Y=H, and R=Et;
croconium dyes, e.g. compound 9 and Table IV on page 30 of Matusoka (supra), i.e.

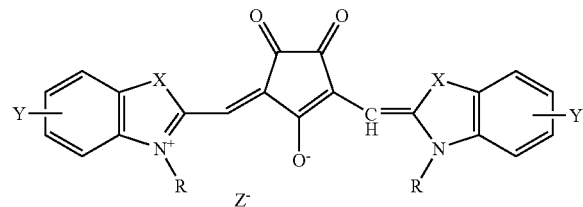

where X=CH=CH, Y=H, and R=Et,
X=S, Y=H, and R=Et,
X=CMe₂, Y=H, and R=Me,
and compound 7, page 26, of Matsuoka (supra), i.e.

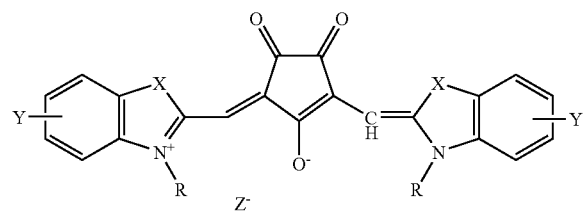

where X=CH=CH, Y=H, and R=Et;
azulenium dyes, e.g. compound 8 on page 27 of Matsuoka (supra), i.e.

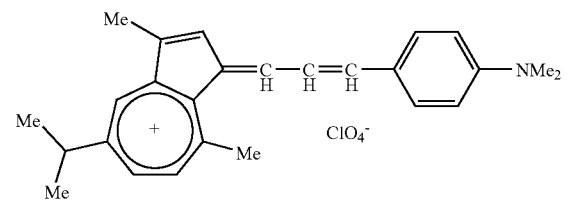

merocyanine dyes, e.g. compound 16, R=Me, on page 32 of Matsuoka (supra), i.e.

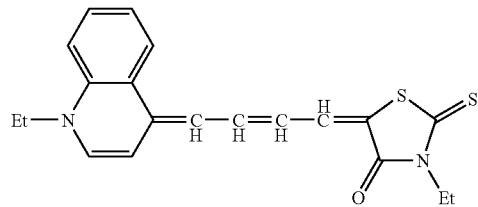

indoaniline dyes such as copper and nickel complexes of indoaniline dyes, e.g. compound 6 on page 63 of Matsuoka (supra), i.e.

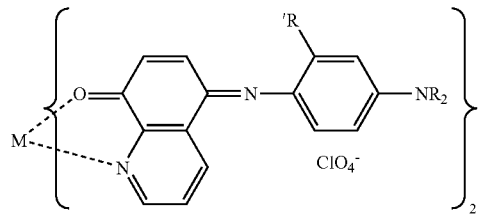

where R=Et, R'=Me, M=Cu,
R=Et, R'=Me, M=Ni,
R=Me, R'=H, M=Cu, or
R=Me, R'=H, M=Ni,
benzo[a]phenoxazinium dyes and benzo[a]phenothiazinium dyes, e.g. as shown on page 201 of Matsuoka (supra), i.e.

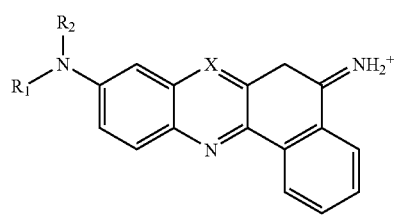

where X=O or S;
1,4-diaminoanthraquinone(N-alkyl)-3'-thioxo-2,3-dicarboximides, e.g. compound 20, on page 41 of Matusoka (supra)

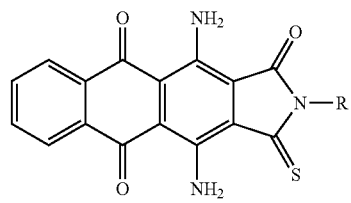

indanthrene pigments, e.g.

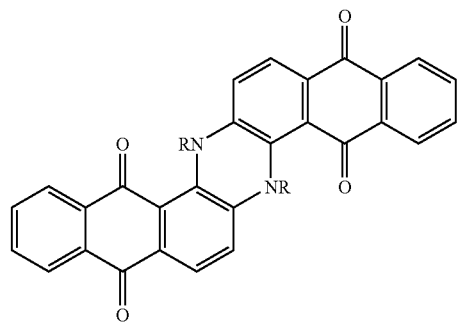

see compound 21 on page 41 of Matsuoka (supra); 2-arylamino-3,4-phthaloylacridone dyes, e.g. compound 22 on page 41 of Matsuoka (supra)

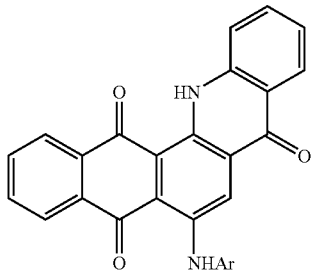

trisphenoquinone dyes, e.g. compound 23 on page 41 of Matsuoka (supra)

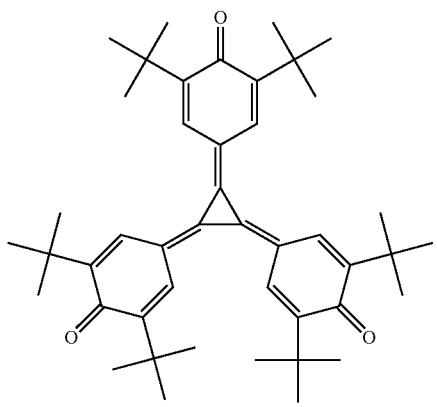

azo dyes, e.g. the monoazo dye, compound 2 on page 90 of Matsuoka (supra), i.e.

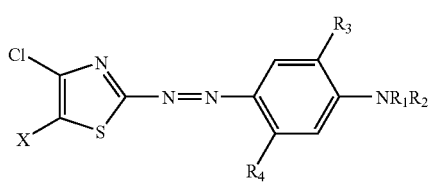

where X=CH=C(CN)$_2$, R$_1$=R$_2$=Et, R$_3$=R$_4$=H, X=C(CN)=C(CN)$_2$, R$_1$=R$_2$=Et, R$_3$=R$_4$=H, or

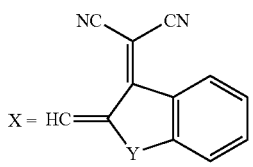

and Y=C=O, R$_1$=R$_2$=Et, R$_3$=R$_4$=H,
or Y=SO$_2$, R$_1$=H, R$_2$=CH(Me)nBu, R$_3$=OMe, and R$_4$=NHAc;
azo dyes, e.g. the polyazo dye, compound 5 on page 91 of Matsuoka (supra), i.e.

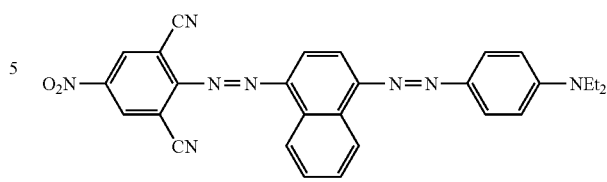

intramolecular charge transfer donor-acceptor infrared dyes, e.g. compounds 6 and 7 on page 91 of Matsuoka (supra), i.e.

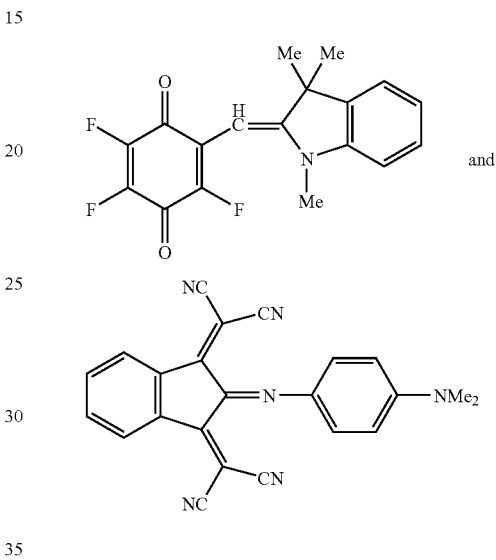

and nonbenzenoid aromatic dyes, e.g. compound 8, a tropone, on page 92, of Matsuoka (supra), i.e.

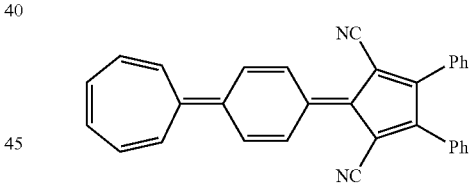

tetrazine radical dyes, e.g. compound 9 on page 92 of Matsuoka (supra), i.e.

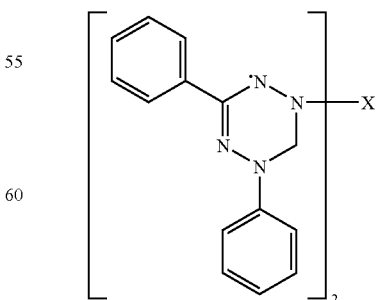

in which, X=p-phenylene or

X=p-terphenylene as well as compound 10 on page 92 of Matsuoka (supra), i.e.

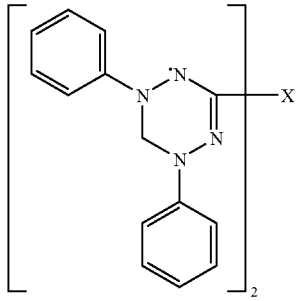

in which X=p-biphenyl;

cationic salts of tetrazine radical dyes, e.g. compound 11 on page 92 of Matsuoka (supra)

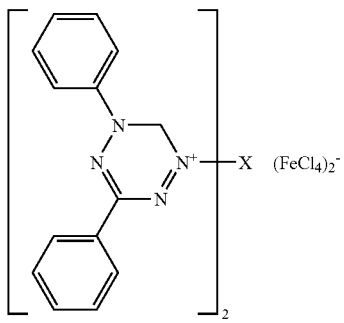

in which X=p-phenylenel;

donor-acceptor intermolecular charge transfer dyes, e.g. CT complexes of compounds 13b and 14a to 14c on page 93 of Matsuoka (supra), i.e.

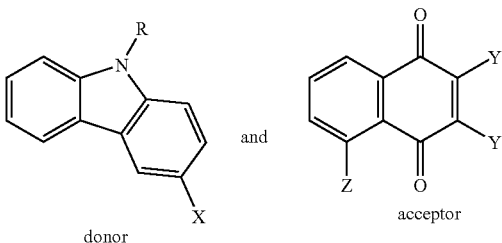

where X=CH=N—N(Ph)$_2$ in the donor and
a) Y=CN, Z=NO$_2$
b) Y=CN, Z=H or
a) Y=Cl, Z=NO$_2$ in the acceptor;

anthraquinone dyes, e.g. compounds 12 (X=S or Se) on page 38 of Matsuoka (supra), i.e.

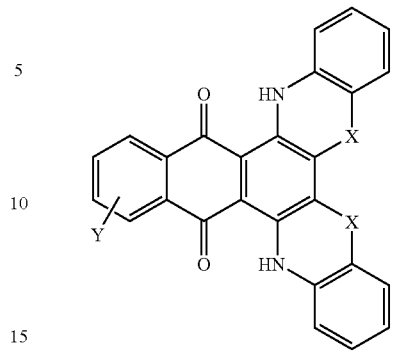

wherein X=S or Se and Y=tetrachloro, tetrabromo, 2,3-dicarboxylic acid, 2,3-dicarboxylic anhydride, or 2,3-dicarboxylic acid N-phenyl imide;

naphthoquinone dyes, e.g. compounds 2, 3, and 4 on page 37, of Matsuoka (supra), i.e.

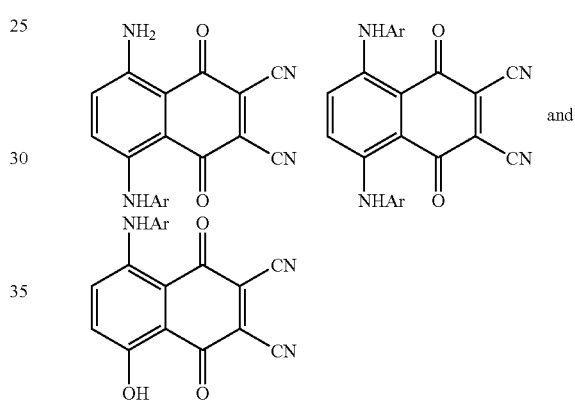

metalated azo dyes such as azo dyes containing nickel, cobalt, copper, iron, and manganese;

phthalocyanine dyes, e.g. compound 1 in Table II on page 51 of Matsuoka (supra), e.g.

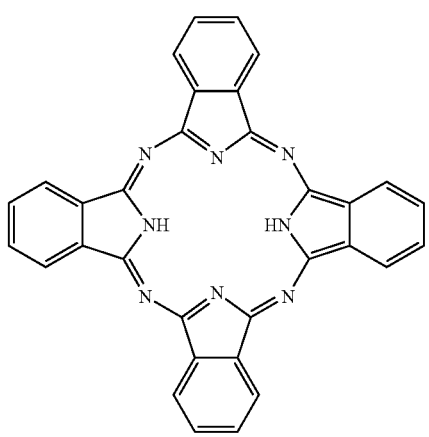

naphthalocyanine dyes, e.g. compound 3 in Table II on page 51 of Matsuoka (supra), e.g.

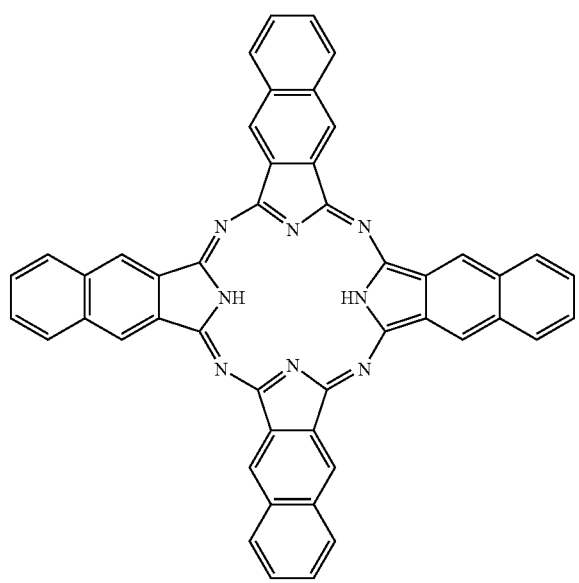

metal phthalocyanines such as phthalocyanines containing aluminum, silicon, nickel, zinc, lead, cadmium, magnesium, vanadium, cobalt, copper, and iron, e.g. compound 1 in Table III on page 52 of Matsuoka (supra), e.g.

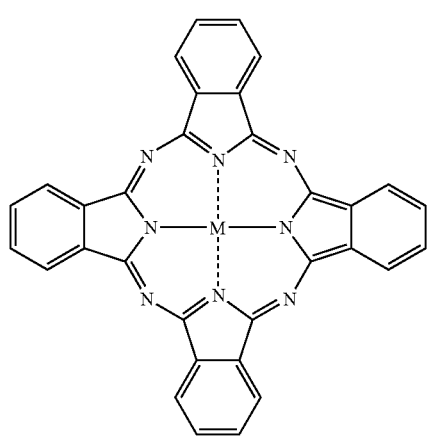

in which, for example, M=Mg;

metal naphthalocyanines such as naphthalocyanines containing aluminum, zinc, cobalt, magnesium, cadmium, silicon, nickel, vanadium, lead, copper, and iron, see compound 3 in Table III on page 52 of Matsuoka (supra), e.g.

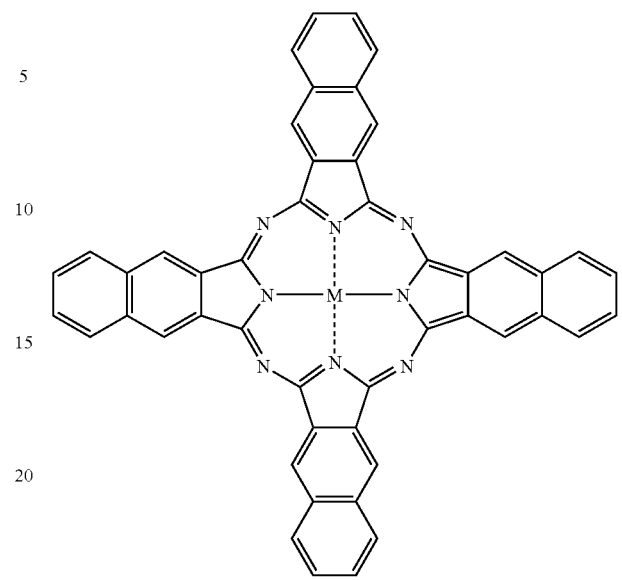

in which, for example, M=Mg;

bis(dithiolene) metal complexes comprising a metal ion such as nickel, cobalt, copper, and iron coordinated to four sulfur atoms in a bis(S,S=-bidentate) ligand complex, e.g. see Table I on page 59 of Matsuoka (supra)

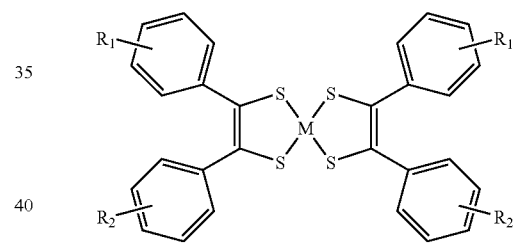

where
$R_1=R_2=CF_3$, M=Ni,
$R_1=R_2$=phenyl, M=Pd,
$R_1=R_2$=phenyl, M=Pt,
$R_1$=C4 to C10 alkyl, $R_2$=H, M=Ni,
$R_1$=C4 to C10 alkyl, $R_2$=H, M=Pd,
$R_1$=C4 to C10 alkyl, $R_2$=H, M=Pt,
$R_1=R_2$=phenyl, M=Ni,
$R_1=R_2$=p-$CH_3$-phenyl, M=Ni,
$R_1=R_2$=p-$CH_3O$-phenyl, M=Ni,
$R_1=R_2$=p-Cl-phenyl, M=Ni,
$R_1=R_2$=p-$CF_3$-phenyl, M=Ni,
$R_1=R_2$=3,4,-diCl-phenyl, M=Ni,
$R_1=R_2$=o-Cl-phenyl, M=Ni,
$R_1=R_2$=o-Br-phenyl, M=Ni,
$R_1=R_2$=3,4,-diCl-phenyl, M=Ni,
$R_1=R_2$=p-$CH_3$, M=Ni,
$R_1=R_2$=2-thienyl, M=Ni,
$R_1$=p-$(CH_3)_2$ N-phenyl, $R_2$=phenyl, M=Ni, and
$R_1$=p-$(CH_3)_2$ N-phenyl, $R_2$=p-$H_2$N-phenyl, M=Ni;
bis(benzenedithiolate) metal complexes comprising a metal ion such as nickel, cobalt, copper, and iron coordinated to four sulfur atoms in a ligand complex, e.g. see Table III on page 62 of Matsuoka (supra), i.e.

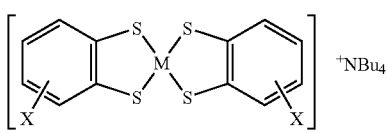

where

X=tetramethyl, M=Ni,

X=4,5-dimethyl, M=Ni,

X=4-methyl, M=Ni,

X=tetrachloro, M=Ni,

X=H, M=Ni,

X=4-methyl, M=Co,

X=4-methyl, M=Cu, and

X=4-methyl, M=Fe;

N,O-bidentate indoaniline dyes comprising a metal ion such as nickel, cobalt, copper, and iron coordinated to two nitrogen and two oxygen atoms of two N,O-bidentate indoaniline ligands, e.g. compound 6 in Table IV on page 63 of Matsuoka (supra), e.g.

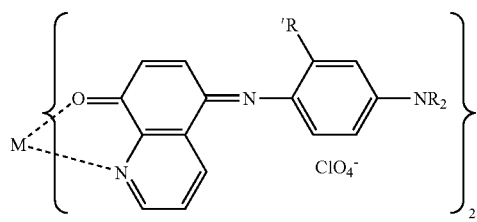

where R=Et, R'=Me, M=Cu,

R=Et, R'=Me, M=Ni,

R=Me, R'=H, M=Cu, and

R=Me, R'=H, M=Ni, bis(S,O-dithiolene) metal complexes comprising a metal ion such as nickel, cobalt, copper, and iron coordinated to two sulfur atoms and two oxygen atoms in a bis(S,O-bidentate) ligand complex, e.g. see U.S. Pat. No. 3,806,462, e.g.

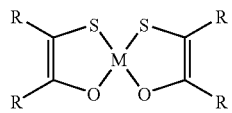

a-diimine-dithiolene complexes comprising a metal ion such as nickel, cobalt, copper, and iron coordinated to two sulfur atoms and two imino-nitrogen atoms in a mixed S,S— and N,N-bidentate diligand complex, e.g. see Table II on page 180, second from bottom, of Matsuoka (supra) (also see Japanese patents: 62/39,682, 63/126,889 and 63/139,303), e.g.

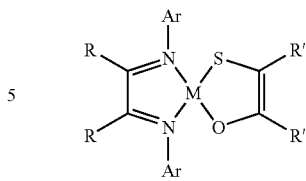

and tris(a-diimine) complexes comprising a metal ion coordinated to six nitrogen atoms in a triligand complex, e.g. see Table II on page 180 of Matsuoka (supra), last compound, (also see Japanese Patents 61/20,002 and 61/73,902), e.g.

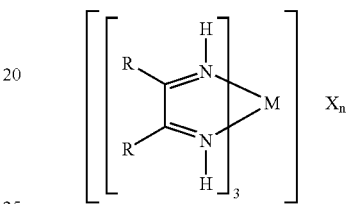

Representative examples of visible dyes include fluorescein derivatives, rhodamine derivatives, coumarins, azo dyes, metalizable dyes, anthraquinone dyes, benzodifuranone dyes, polycyclic aromatic carbonyl dyes, indigoid dyes, polymethine dyes, azacarbocyanine dyes, hemicyanine dyes, barbituates, diazahemicyanine dyes, stryrl dyes, diaryl carbonium dyes, triaryl carbonium dyes, phthalocyanine dyes, quinophthalone dyes, triphenodioxazine dyes, formazan dyes, phenothiazine dyes such as methylene blue, azure A, azure B, and azure C, oxazine dyes, thiazine dyes, naphtholactam dyes, diazahemicyanine dyes, azopyridone dyes, azobenzene dyes, mordant dyes, acid dyes, basic dyes, metallized and premetallized dyes, xanthene dyes, direct dyes, leuco dyes which can be oxidized to produce dyes with hues bathochromically shifted from those of the precursor leuco dyes, and other dyes such as those listed by Waring, D. R. and Hallas, G., in AThe Chemistry and Application of Dyes=, Topics in Applied Chemistry, Plenum Press, New York, N.Y., 1990. Additonal dyes can be found listed in Haugland, R. P., "Handbook of Fluorescent Probes and Research Chemicals", Sixth Edition, Molecular Probes, Inc., Eugene Oreg., 1996.

Such chormophores and fluorophores may be covalently linked either directly to the vector or to or within a linker structure. Once again linkers of the type described above in connection with the metal reporters may be used for organic chromophores or fluorophores with the chromophores/fluorophores taking the place of some or all of the chelant groups.

As with the metal chelants discussed above chromophores/fluorophores may be carried in or on a particulate linker-moieties, eg. in or on a vesicle or covalently bonded to inert matrix particles that can also function as a light scattering reporter.

Particulate Reporters or Linker-Reporters

The particulate reporters and linker-reporters generally fall into two categories—those where the particle comprises a matrix or shell which carries or contains the reporter and those where the particle matrix is itself the reporter. Examples of the first category are: vesicles (eg. micelles, liposomes, microballoons and microbubbles) containing a liquid, gas or solid phase which contains the contrast effective reporter, eg. an echogenic gas or a precursor therefor (see for example GB 9700699.3), a chelated paramagnetic metal or radionuclide, or a water-soluble iodinated X-ray contrast agent; porous particles loaded with the reporter, eg. paramagnetic metal loaded molecular sieve particles; and solid particles, eg. of an inert biotolerable polymer, onto which the reporter is bound or coated, eg. dye-loaded polymer particles.

Examples of the second category are: light scattering organic or inorganic particles; magnetic particles (ie. superparamagnetic, ferromagnetic or ferrimagnetic particles); and dye particles.

Preferred particulate reporters or reporter-linkers include superparamagnetic particles (see U.S. Pat. No. 4,770,183, WO97/25073, WO96/09840, etc.), echogenic vesicles (see WO92/17212, WO97/29783, etc.), iodine-containing vesicles (see WO95/26205 and GB9624918.0), and dye-loaded polymer particles (see WO96/23524).

The particulate reporters may have one or more vectors attached directly or indirectly to their surfaces. Generally it will be preferred to attach a plurality (eg. 2 to 50) of vector moieties per particle. Particularly conveniently, besides the desired targeting vector, one will also attached flow decelerating vectors to the particles, ie. vectors which have an affinity for the capillary lumen or other organ surfaces which is sufficient to slow the passage of the contrast agent through the capillaries or the target organ but not sufficient on its own to immobilise the contrast agent.

Such flow decelerating vectors (described for example in GB9700699.3) may moreover serve to anchor the contrast agent once it has bound to its target site.

The means by which vector to particle attachment is achieved will depend on the nature of the particle surface. For inorganic particles, the linkage to the particle may be for example by way of interaction between a metal binding group (eg. a phosphate, phosphonate or oligo or polyphosphate group) on the vector or on a linker attached to the vector. For organic (eg. polymeric) particles, vector attachment may be by way of direct covalent bonding between groups on the particle surface and reactive groups in the vector, eg. amide or ester bonding, or by covalent attachment of vector and particle to a linker. Linkers of the type discussed above in connection with chelated metal reporters may be used although in general the linkers will not be used to couple particles together. For non-solid particles, eg. droplets (for example of water insoluble iodinated liquids as described in U.S. Pat. No. 5,318,767, U.S. Pat. No. 5,451,393, U.S. Pat. No. 5,352,459 and U.S. Pat. No. 5,569,448) and vesicles, the linker may conveniently contain hydrophobic "anchor" groups, for example saturated or unsaturated $C_{12-30}$ chains, which will penetrate the particle surface and bind vector to particle. Thus for phospholipid vesicles, the linker may serve to bind the vector covalently to a phospholipid compatible with the vesicle membrane. Examples of linker binding to vesicles and inorganic particles are described in GB9622368.0 and WO97/25073.

Besides the vectors, other groups may be bound to the particle surface, eg. stabilisers (to prevent aggregation) and biodistribution modifiers such as PEG. Such groups are discussed for example in WO97/25073, WO96/09840, EP-A-284549 and U.S. Pat. No. 4,904,479.

Preferably the V-L-R agents of the invention will have non-peptidic vectors (such as losartan) coupled directly or indirectly to a reporter, eg. with covalently bound iodine radioisotopes, with metal chelates attached directly or via an organic linker group or coupled to a particulate reporter or linker-reporter, eg. a superparamagnetic crystals (optionally coated, eg. as in WO97/25073), or a vesicle, eg. a gas containing or iodinated contrast agent containing micelle, liposome or microballoon.

All of the publications referred to herein are incorporated herein by reference.

The agents of the invention may be administered to patients for imaging in amounts sufficient to yield the desired contrast with the particular imaging technique. Where the reporter is a metal, generally dosages of from 0.001 to 5.0 mmoles of chelated imaging metal ion per kilogram of patient bodyweight are effective to achieve adequate contrast enhancements. For most MRI applications preferred dosages of imaging metal ion will be in the range of from 0.02 to 1.2 mmoles/kg bodyweight while for X-ray applications dosages of from 0.05 to 2.0 mmoles/kg are generally effective to achieve X-ray attenuation. Preferred dosages for most X-ray applications are from 0.1 to 1.2 mmoles of the lanthanide or heavy metal compound/kg bodyweight. Where the reporter is a radionuclide, dosages of 0.01 to 100 mCi, preferably 0.1 to 50 mCi will normally be sufficient per 70 kg bodyweight. Where the reporter is a superparamagnetic particle, the dosage will normally be 0.5 to 30 mg Fe/kg bodyweight. Where the reporter is a gas or gas generator, eg. in a microballoon, the dosage will normally be 0.05 to 100 µL gas per 70 kig bodyweight.

The dosage of the compounds of the invention for therapeutic use will depend upon the condition being treated, but in general will be of the order of from 1 pmol/kg to 1 mmol/kg bodyweight.

The compounds of the present invention may be formulated with conventional pharmaceutical or veterinary aids, for example emulsifiers, fatty acid esters, gelling agents, stabilizers, antioxidants, osmolality adjusting agents, buffers, pH adjusting agents, etc., and may be in a form suitable for parenteral or enteral administration, for example injection or infusion or administration directly into a body cavity having an external escape duct, for example the gastrointestinal tract, the bladder or the uterus. Thus the compounds of the present invention may be in conventional pharmaceutical administration forms such as tablets, capsules, powders, solutions, suspensions, dispersions, syrups, suppositories etc. However, solutions, suspensions and dispersions in physiologically acceptable carrier media, for example water for injections, will generally be preferred.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

For imaging of some portions of the body the most preferred mode for administering contrast agents is parenteral, e.g., intravenous administration. Parenterally administrable forms, e.g. intravenous solutions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the chelates and which will not interfere with the manufacture, storage or use of products.

The agents of formula I may be therapeutically effective in the treatment effective in the treatment of disease states as well as detectable in in vivo imaging. Thus for example the vector on the reporter moieites may have therapeutic efficacy, eg. by virtue of the radiotherapeutic effect of a radionuclide reporter, the efficacy in photodynamic therapy of a chromophore (or fluorophore) reporter or the chemotherapeutic effect of the vector moiety.

Use of the agents of formula I in the manufacture of therapeutic compositions and in methods of therapeutic or prophylactic treatment of the human or non-human animal body are thus considered to represent further aspects of the invention.

In one embodiment, the contrast agent of the invention conveniently comprises a gas-containing or gas-generating material, preferably in suspension in an aqueous carrier material and conjugated to one or more vectors of which at least one is a vector V as defined above, eg. an AII receptor antagonist such as CV11974 or TCV-116. The gas may take the form of microbubbles stabilised by a monolayer of a film-forming surfactant, or stabilised by a matrix material other than a surfactant. The vectors may be for example coupled to such surfactant or matrix and may be bioactive or non-bioactive. The vectors may have different targeting specificities and in one preferred embodiment are such as to interact with their receptors but not to fixedly bind the gas-containing vesicles.

The present invention will now be further illustrated by way of the following non-limiting examples. Unless otherwise indicated, all percentages given are by weight.

EXAMPLE 1

Angiotensin Receptor Binding Contrast Agent for MR Imaging

Compound 1

Diethylenetriamine-pentaacetic acid dianhydride (53.8 g, 137 mmol) is dissolved in dry DMF (N,N-dimethylformamide) and 4'-[3-(3-aminopropyl)-5-butyl-1H-1,2,4-triazol-1-yl)methyl][1,1'-biphenyl]-2-carboxylic acid (prepared in accordance with WO91/17148, 5 g, 13.7 mmol) dissolved in dry DMF is added. The reaction mixture is stirred at elevated temperature under nitrogen atmosphere. The reaction is followed by TLC. The solvent is rotary evaporated and the substance purified by chromatography.

Gd(III) Chelate of Compound 1

To a solution of compound 1(2 g, 2.7 mmol) in water is added gadolinium oxide $Gd_2O_3$(0.5 g, 1.4 mmol) and the mixture is heated at 95° C. After filtration the solution is evaporated and dried in vacuo at 50° C.

EXAMPLE 2

Angiotensin Receptor Binding Contrast Agent for Nuclear Medicine

Tc99m Chelate of Compound 1

Compound 1 from Example 1 (1 mg) is dissolved in 0.1 N NaOH, $SnCl_2 2H_2O$ (100 Φg) dissolved in 0.05 N HCl and a solution of 10–100 mCi Tc99m in the form of sodium pertechnetate in saline is added. The pH of the solution is adjusted to pH 7–8 by addition of 0.5 M phosphate buffer (pH 5) after less than one minute. The reaction is followed by TLC and the substance is purified by chromatography.

EXAMPLE 3

Angiotensin Receptor Binding Contrast Agent for Nuclear Medicine

An aqueous solution of $^{131}I_2$ (2 equivalents) and sodium perchlorate (1 equivalent) is added to an aqueous solution of 4'-[3,5-dibutyl-1H-1,2,4-triazole-1-yl)methyl][1,1'-biphenyl]-2-carboxylic acid (prepared in accordance with WO91/17148, (1 equivalent). The solvent is rotary evaporated and the substance is purified by chromatography.

EXAMPLE 4

Angiotensin Receptor Binding Contrast Agent For Ultrasound and Scattering Light Imaging Compound 2

Succinic anhydride (2.7 g, 27.4 mmol) is dissolved in dry DMF and 4'-[3-(3-aminopropyl)-5-butyl-1H-1,2,4-trizol-1-yl)methyl][1,1'-biphenyl]-2-carboxylic acid (prepared in accordance with WO91/17148, 5 g, 13.7 mmol) dissolved in dry DMF is added. The reaction mixture is stirred at elevated temperature under nitrogen atmosphere. The reaction is followed by TLC. The solvent is rotary evaporated and the substance is purified by chromatography.

Compound 3

DSPE (distearoylphosphatidylethanolamine) (0.5 g, 0.7 mmol) is added to a solution of Compound 2 (0.3 g, 0.7 mmol) and DCC (N,N'-dicyclohexylcarbodiimide) in dry DMF. The reaction mixture is stirred at ambient temperature and the reaction is followed by TLC. The dispersion is left over night +4° C. The dispersion is filtered and the solvent rotary evaporated before the substance is purified by chromatography.

Gas Containing Micro Articles Comprising Phosphatidyleserine and Compound 3

To phosphatidylserine (5 mg) is added 5% propylenglycol-glycerol in water (1 ml). The dispersion is heated to not more than 90° C. for 5 minutes and then cooled to ambient temperature. The dispersion (0.8 ml) is transferred to a vial (1 ml) and compound 3 (0.1–1.0 mb) is added. The vial is put on a roller table for some hours. The head space of the vial is flushed with perfluorobutane. The vial is shaken in a cap-mixer for 45 seconds, whereafter the sample is put on a roller table. After centrifugation the infranatant is exchanged with water. The washing procedure is repeated 2–3 times.

EXAMPLE 5

Tc Labelled angiotensin receptor binding contrast agent for scintigraphy: Tc chelate of 2-(4-N-(MAG-3)-aminophenyl)-1-benzyl-4-chloro-imidazole-5-acetic acid hydrochloride 2-Amino-3,3-dichloropropenonitrile (Compound 4)

A solution of dichloroacetonitrile (55.0 g, 0.50 mole) and acetone cyanohydrin (46.8 g, 0.55 mole) in acetonitrile (200 ml) and diethyl ether (50 ml) was cooled to 0 EC. Potassium cyanide (10.65 g, 10.0 mmol) was added, and the mixture was stirred under nitrogen atmosphere for 19 hours at 0 EC. The solution was evaporated, the brown residue was dissolved in diethyl ether (125 ml), treated with active carbon, filtered and evaporated. The residue was mixed with diethyl ether (30 ml) and hexanes (30 ml). The title compound, Compound 4, was isolated by filtration.

Yield 21.2 g (light yellow crystals)

The filtrate was evaporated, the residue was washed with ether/hexanes (1:1, 20 ml). More of the title compound was isolated by filtration.

Total yield: 34.5 g (50%) m.p. 56–58 EC.

NMR confirmed the structure of the title compound (~10% of cyanohydrin starting material as impurity).

2-(4-Nitrobenzylidene)amino-3,3-dichloropropenonitrile (Compound 5)

A solution of 2-amino-3,3-dichloropropenonitrile (15.0 g, 0.11 mole) and 4-nitrobenzaldehyde (15.1 g, 0.10 mmol) in toluene (200 ml) was refluxed for 23 hours. The mixture was evaporated, methanol (100 ml) was added and the mixture was allowed to stand overnight. After filtration, the title compound was isolated as a brown-yellow solid.

Yield 15.0 g, m.p. 171–174 EC

Rf=0.9 (silica, ethyl acetate:hexane=1:2)

Evaporation of the mother liquor gave 13.7 g brown residue. Methanol (25 ml) was added and the mixture was allowed to stand for 2 days. Filtration left 6.6 g dark brown material (title compound—Compound 5).

Total yield: 21.6 g (80%)

NMR confirmed the structure of the title compound.

4-chloro-5-formyl-2-(4-nitrophenyl)imidazole (Compound 6)

HCl gas was bubbled through a solution of 2-(4-nitrobenzylidene)amino-3,3-dichloro-propenonitrile (40.0 g, 0.148 mole) in dioxane (500 ml) at room temperature. The mixture was stirred for 23 hours at 50 EC. HCl gas was bubbled through followed by stirring for 24 hours at 50 EC. The mixture was stirred for 8 more days at 50 EC with addition of HCl-gas every 24 hours, followed by stirring at 50 EC for 4 more days. More HCl-gas was added and stirred for 3 more days at 50 EC. The solution was cooled to 0 EC and filtered. The residue was mixed with ethanol (96%, 200 ml) and the title compound, Compound 6, was isolated by filration. Yield: 23.1 g (62%). NMR confirmed the structure of the title compound.

1-Benzyl-4-chloro-5-formyl-2-(4-nitrophenyl)imidazole (Compound 7)

A mixture of 4-chloro-5-formyl-2-(4-nitrophenyl)imidazole (19.7 g, 78.3 mmol), benzyl bromide (14.5 g, 85.0 mmole) and potassium carbonate (11.7 g, 85.0 mmole) in DMF (150 ml) was heated to 110 EC for 1.5 hours. The mixture was evaporated and residue was poured into cold water and was allowed to stay overnight in the refrigerator. The tarry residue was pulverized and filtered. Yield of crude title compound: 33.4 g. The product was recrystallized from ethanol (96%, 350 ml).

Yield: 14.0 g. NMR confirmed the structure of the title compound, Compound 7.

1-Benzyl-4-chloro-5-(hydroxymethyl)-2-(4-nitrophenyl) imidazole (Compound 8)

Sodium borohydride (1.1 g, 29 mmole) was added in three portions to a stirred mixture of crude 1-benzyl-4-chloro-5-formyl-2-(4-nitrophenyl)imidazole (54.2 g, 88 mmole) in methanol (250 ml) at room temperature. After two hours, more sodium borohydride (0.51 g, 15 mmol) was added, the mixture was stirred for 30 minutes and the methanol was evaporated. The residue was mixed with water (250 ml) and extracted with methylene chloride (200 ml, 3×50 ml). The combined organic solutions were washed with water (2×50 ml) and dried ($NaSO_4$) overnight.

The mixture was filtered and evaporated leaving 20.9 g residue. The title compound, Compound 8, was purified by flash chromatography (150×65 mm silica gel 60 column eluted with ethyl acetate/hexanes (1:1)). The fractions containing the title compound were evaporated.

Yield: 12.75 g (42%).

Rf=0.4 (silica, ethyle acetate/hexanes (1:1)).

1-Benzyl-4-chloro-5-(chloromethyl)-2(4-nitrophenyl)imidazole (Compound 9)

Thionyl chloride (0.90 ml, 1.48 g, 12.4 mmol) was added dropwise to a stirred suspension of 1-benzyl-4-chloro-5-(hydroxymethyl)-2(4-nitrophenyl)imidazole (18.5 g, 5.4 mmole) in chloroform (15 ml) at room temperature. The brown solution was stirred for 2.5 hours then evaporated to dryness. Toluene (12 ml) was added to the residue and evaporated to dryness. The residue was dissolved in chloroform (20 ml) and used in the next step for introduction of the cyano functional group.

1-Benzyl-4-chloro-2(4-nitrophenyl)-5-imidazolyl acetonitrile (Compound 10)

A solution of sodium cyanide (1.60 g, 32.7 mmol) and tetrabutyl ammonium bromide (0.2 g) in ice water (10 ml) was added dropwise to a vigorously stirred solution of 1-benzyl-4-chloro-5-(chloromethyl)2-(4-nitrophenyl)imidazole (5.4 mmol) in chloroform at 0 EC. The mixture was stirred at 0 EC for 2 hours and then allowed to warm to room temperature, diluted with water (10 ml), the organic layer was washed with water (10 ml). The combined aqueous layers were extracted with chloroform (2×2 ml). The combined organic solutions were dried ($NaSO_4$), filtered and evaporated yielding 4.3 g. The product was purified by flash chromatography (170×25 mm, silica gel 60 column eluted with ethyl acetate/hexanes 1:1). Yield: 2.1 g.

Rf=0.7 (silica, ethyl acetate/hexanes 1:1).

NMR confirmed the structure of the title compound, Compound 10.

1-Benzyl-2-(4-nitrophenyl)-5-imidazole-acetic acid (Compound 11)

A stirred mixture of 1-benzyl-4-chloro-2-(4-nitrophenyl)-5-imidazolyl acetonitrile (2.0 g, 5.4 mmol) in 6M HCl (20 ml) was refluxed for 4 hours. The mixture was diluted with water (100 ml). A yellow oil precipitated which solidified upon cooling to room temperature. Filtration gave 2.2 g solid material which was recrystallized from 96% ethanol (15 ml) and water (10 ml).

Filtration gave 2.24 g moist residue. NMR confirmed the structure of the title compound, Compound 11. The product was used in the next step.

2-(4-aminophenyl)-1-benzyl-4-chloro-imidazole-5-acetic acid hydrochloride (Compound 12)

A mixture of 1-benzyl-2-(4-nitrophenyl)-5-imidazole-acetic acid (2.1 g, 5.0 mmol), 10% palladium on carbon (0.10 g), 12 M HCl (3.0 ml), 96% ethanol (50 ml) and water (50 ml) was hydrogenated at 55 psi for 1.5 hours on a Parr shaker hydrogenation apparatus. The mixture was filtered through a celite pad and then through a fluted filter paper. Evaporation left the title compound, Compound 12, as 1.0 g orange solid.

Rf=0.1 (silica, ethyl acetate/hexanes 1:1).

EXAMPLE 6

$^{131}$I labelled 2-(4-aminophenyl)-1-benzyl-4-chloro-imidazole-5-acetic acid hydrochloride Compound 12 from Example 5 was labelled with $^{131}$I using the Chloramine T method as described in Radioisotopes in Biology. A Practical Approach. (1990) and in Nature 194, (1962) 495.

Labelling yield: 56%.

EXAMPLE 7

Tc Labelled angiotensin receptor binding contrast agent for scintigraphy: Tc chelate of 2-(4-N-(MAG-3)-aminophenyl)-1-benzyl-4-chloro-5-hydroxymethylimidazole 2-(4-aminophenyl)-1-benzyl-4-chloro-5-(hydroxymethyl) imidazole hydrochloride (Compound 14)

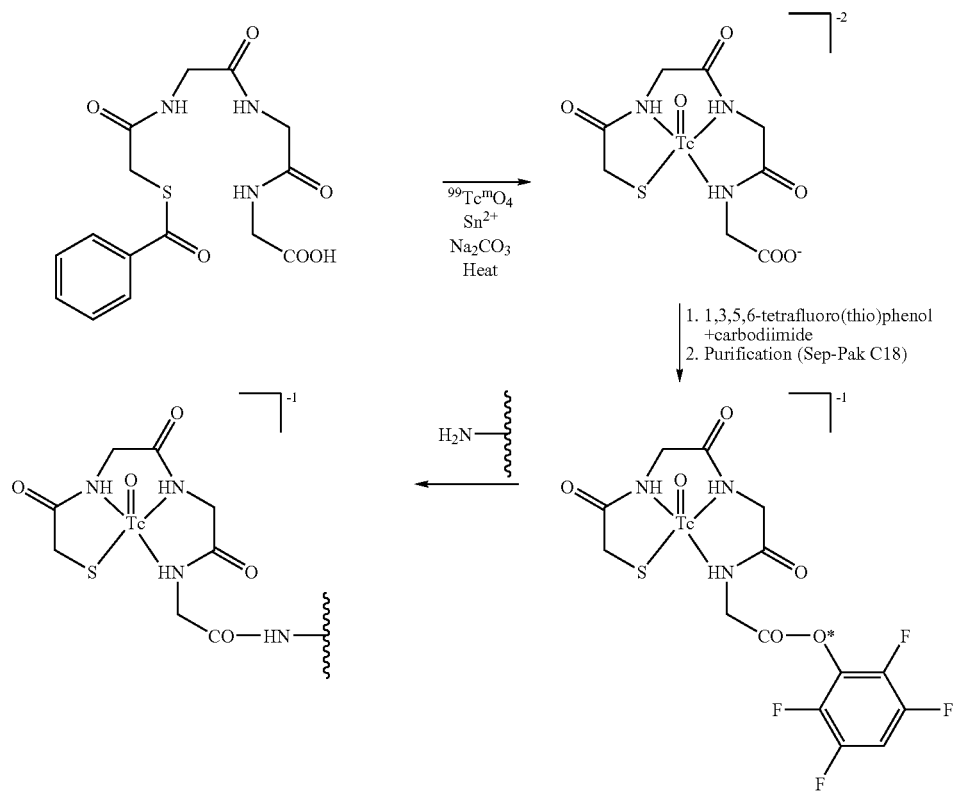

(the *-marked oxygen may be replaced by a sulphur)

Tc chelate of 2-(4-N-(MAG-3)-aminophenyl)-1-benzyl-4-chloro-imidazole-5-acetic acid hydrochloride (Compound 13)

The title compound, Compound 13, was prepared as outlined in the Scheme shown above according to the description in Nuclear Medicine Communications 16, (1995) 942–957.

Labelling yield: >95%

A mixture of 1-benzyl-4-chloro-5-(hydroxymethyl)-2-(4-nitrophenyl)imidazole (1.0 g, 2.8 mmol, Compound 8 from Example 5), 10% palladium on carbon (0.10 g), 12M HCl (1.0 ml) 96% ethanol (50 ml) and water (50 ml) was hydrogenated at 55 psi for 1.5 hours on a Parr shaker hydrogenation apparatus. The mixture was filtered through a celite pad and then through a fluted filter paper. Evaporation left 1.5 g of amber oil.

Rf=0.2 (silica, ethyl acetate/hexanes 1:1).

Tc chelate of 2-(4N-(MAG-3)-aminophenyl)-1-benzyl-4-chloro-5-hydroxymethylimidazole (Compound 15)

The title compound, Compound 15, was prepared as described in Example 5 Compound 13.

Labelling yield: 89%.

EXAMPLE 8

$^{131}$I Labelled N-Benzyl-Losartan

N-Benzyl-Losartan (Compound 16)

Losartan (100 mg/2.22 mmol) was dissolved in 3 ml acetonitrile. Benzylbromide (38 mg) was added, and the reaction mixture was stirred overnight at ambient temperature. The solvent was evaporated in vacuo, and the residue was redissolved in chloroform, filtered and purified by column chromatography. The product was identified by MALDI mass spectrometry and used without further purification.

$^{131}$I Labelled N-Benzyl-Losartan (Compound 17)

The compound was labelled using an exchange labelling technique as described in Radioisotopes in Biology. A practical Approach. (1990) and in Nature 194, (1962) 495

Labelling yield: 98%

EXAMPLE 9

Tc Labelled Losartan derivative for scintigraphy: Tc chelate of N-(N-MAG-3-Glycyl)-Losartan FmocGlycyl-Losartan (Compound 18)

Fmoc-Gly (300 mg/1 mmol) was dissolved in 10 ml THF. DCC (110 mg/0.55 mmol) dissolved in 5 ml THF was added and the reaction mixture was stirred overnight. DCC was removed by filtration and the solvent removed in vacuo.

TLC showed one UV+spot, and the structure was confirmed by MALDI mass spectrometry.

The crude product was dissolved in 10 ml THF and 100 mg Losartan was added. Stirring was continued overnight at ambient temperature. TLC showed full convertion of the starting material. Solvent was removed in vacuo. The crude product was dissolved in chloroform and purified by column chromatography. TLC showed one UV+spot and the structure was confirmed by MALDI mass spectrometry.

Glycyl-Losartan (Compound 19)

100 mg FmocGlycyl-Losartan (Compound 18) was dissolved in 5 ml 10% piperidine/DMF and stirred for 30 minutes. TLC showed full convertion of the UV+ starting material to a new UV+, Ninhydrine+ spot. The solvent was evaporated in vacuo. The structure was confirmed by MALDI mass spectrometry and the crude product used without further purification.

Tc chelate of N-(N-MAG-3-Glycyl)-Losartan (Compound 20)

The title compound, Compound 20, was prepared as described in Example 5, Compound 13.

Labelling yield: 80%

EXAMPLE 10

Multiple-specific Gas-containing Microbubbles Encapsulated with Phosphatidylserine and Biotin-PEG$_{3400}$-alanyl-cholesterol and Functionalised with Streptavidin/biotinyl-endothelin-1 Peptide (Biotin-D-Trp-Leu-Asp-Ile-Ile-Trp.OH) and Biotinyl-fibrin-anti-polymerant Peptide (Biotin-GPRPPER-HQS.NH$_2$)

This example is directed at the preparation of targeted ultrasound microbubbles whereby streptavidin is used as a linker between biotinylated reporter(s) and vector(s).

a) Synthesis of Biotin-PEG$_{3400}$-β-Alanine Cholesterol

To a solution of cholesteryl-β-alanine hydrochloride (15 mg, 0.03 mmol) in 3 mL chloroform/wet methanol (2.6:1), was added triethylamine (42 mL, 0.30 mmol). The mixture was stirred for 10 minutes at room temperature and a solution of biotin-PEG$_{3400}$-NHS (100 mg, 0.03 mmol) in 1,4-dioxan (1 mL) was added dropwise. After stirring at room temperature for 3 hours, the mixture was evaporated to dryness and the residue purified by flash chromatography to give white crystals, yield, 102 mg (89%). The structure was verified by MALDI-MS and NMR.

b) Synthesis of Biotinylated Endothelin-1 Peptide (Biotin-D-Trp-Leu-Asp-Ile-Ile-TrP.OH)

The peptide was synthesised on a ABI 433A automatic peptide synthesiser starting with Fmoc-Trp(Boc)-Wang resin (Novabiochem) on a 0.1 mmol scale using 1 mmol amino acid cartridges. All amino acids were preactivated using HBTU before coupling. The simultaneous removal of peptide from the resin and side-chain protecting groups was carried out in TFA containing 5% anisole and 5% H$_2$O for 2 hours giving a crude product yield of 75 mg. Purification by preparative HPLC (Vydac 218TP1022 column) of a 20 mg aliquot of crude material was carried out using a gradient of 30 to 80% B over 40 minutes (A=0.1% TFA/water and B=0.1% TFA/acetonitrile) and a flow rate of 9 mL/min. After lyophilisation of the pure fractions, 2 mg of pure material was obtained (Analytical HPLC; Gradient, 30–80% B where B=0.1% TFA/acetonitrile, A=0.01% TFA/water: column—Vydac 218TP54: Detection—UV 214 nm—product retention time=12.6 minutes). Further product characterisation was carried out using MALDI mass spectrometry; expected, M+H at 1077, found, 1077.

c) Synthesis of Biotinyl-fibrin-anti-polymerant Peptide (Biotin-GPRPPERHQS.NH$_2$)

This peptide was synthesised and purified using similar protocols to those described in section b) above. The pure product was characterised by HPLC and MALDI MS.

d) Preparation of Multiple-specific Gas-filled Microbubbles Encapsulated with Phosphatidylserine and Biotin-PEG$_{1400}$-β-Alanine Cholesterol DSPS (Avanti, 4.5 mg) and biotin-PEG$_{3400}$-β-Alanine cholesterol from section a) (0.5 mg) were weighed into a vial and 0.8 mL of a solution of 1.4% propylene glycol/2.4% glycerol was added. The mixture was warmed to 80 EC for 5 minutes (vials shaken during warming). The sample was cooled to room temperature and the head space flushed with perfluorobutane gas. The vial was shaken in a cap mixer for 45 seconds and the microbubbles rolled overnight. The microbubble suspension was washed several times with deionised water and analysed by Coulter counter and acoustic attenuation.

e) Conjugation with Fluorescein Labelled Streptavidin and Biotinylated Peptides from Section b) and c)

To the microbubble preparation from d) was added fluorescein conjugated streptavidin (0.2 mg) dissolved in PBS (1 mL). The bubbles were placed on a roller table for 3 hours at room temperature. Following extensive washing with water and analysis by fluorescence microscopy, the microbubbles were incubated in 1 mL of PBS containing biotinyl-Endothelin-1 peptide (0.5 mg) and biotinyl-Fibrin-anti-polymerant peptide (0.5 mg) from sections b) and c) respectively for 2 hours. Extensive washing of the microbubbles was performed to remove unconjugated peptide.

EXAMPLE 11

Multiple-specific Gas-filled Microbubbles Encapsulated with Phosphatidylserine and a Biotinylated Lipopeptide Used to Prepare a Streptavidin 'Sandwich' with a Mixture of Biotinyl-endothelin-1 Peptide (Biotin-D-Trp-Leu-Asp-Ile-Ile-Trp.OH) and Biotinyl-fibrin-anti-polymerant Peptide (Biotin-GPRPPERHQS.NH$_2$)

a) Synthesis of Lipopeptide Dipalmitoyl-lysinyl-tryptophanyl-lysinyl-lysinyl-lysinyl(Biotinyl)-glycine The lipopeptide was synthesised on a ABI 433A automatic peptide synthesiser starting with Fmoc-Gly-Wang resin (Novabiochem) on a 0.1 mmol scale using 1 mmol amino acid cartridges. All amino acids and palmitic acid were preactivated using HBTU before coupling.

The simultaneous removal of peptide from the resin and side-chain protecting groups was carried out in TFA containing 5% phenol, 5% EDT, 5% anisole and 5% H$_2$O for 2 hours giving a crude product yield of 150 mg. Purification by preparative HPLC (Vydac 218TP1022 column) of a 40 mg aliquot of crude material was carried out using a gradient of 70 to 100% B over 30 minutes (A=0.1% TFA/water and B=MeOH) at a flow rate of 9 mL/min. After lyophilisation 14 mg of pure material (Analytical HPLC; Gradient, 70–100% B where B=MeOH, A=0.01% TFA/water: column—Vydac 218TP54: Detection—UV 260 and fluorescence, Ex280, Em350—product rection time=22 minutes). Further product characterisation was carried out using MALDI mass spectrometry; expected, M+H at 1478, found, 1471.

b) Preparation of Gas-containing Microbubbles of DSPS 'doped' with the Biotinylated Lipopeptide Sequence from Section a)

DSPS (Avanti, 4.5 mg) and lipopeptide from a) (0.5 mg) were weighed into each of 2 vials and 0.8 mL of a solution of 1.4% propylene glycol/2.4% glycerol was added to each vial. The mixture was warmed to 80 EC for 5 minutes (vials shaken during warming). The samples were cooled to room temperature and the head space flushed with perfluorobutane gas. The vials were shaken in a cap mixer for 45 seconds and the microbubbles formed rolled overnight. The microbubbles were washed several times with deionised water and analysed by Coulter counter and acoustic attenuation.

MALDI mass spectral analysis was used to confirm incorporation into DSPS microbubbles.

c) Preparation of Multiple-specific Gas-filled Microbubbles Encapsulated with Phosphatidylserine and a Biotinylated Lipopeptide and Functionalised with Streptavidin/biotinyl-endothelin-1 Peptide (Biotin-D-Trp-Leu-Asp-Ile-Ile-Trp.OH)/Biotinyl-Fibrin-Anti-polymerant Peptide (Biotin-GPRPPERHOS.NH$_2$)

The microbubble preparation from b) above was treated in an analogous manner to that described in Example 10 section e).

The invention claimed is:

1. A composition of matter of formula I $$V\text{-}L\text{-}R \quad \text{(I)}$$

where V is a non-peptidic organic group having binding affinity for an angiotensin II receptor site, V being the residue of a compound of formula IV

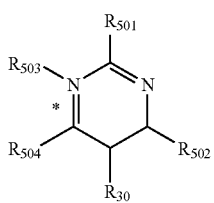

(IV)

where $R_{501}$ is an optionally fluorinated $C_{1-6}$ alkyl group,
$R_{504}$ is an optionally fluorinated $C_{1-6}$ alkyl group,
$R_{502}$ is a carboxy, hydroxy-$C_{1-6}$ alkyl or CHO group; or the double bond marked with an asterisk is replaced by a single bond and $R_{504}$ is an =O or =$NR_{505}$ group, $R_{502}$ is an optionally fluorinated $C_{1-6}$ alkyl group and $R_{503}$ is a carboxyphenyl group and $R_{505}$ is a $C_{1-6}$ alkyl group;
and $R_{30}$ is

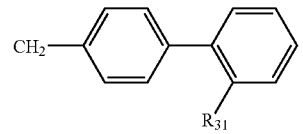

and $R_{31}$ is COOH, tetrazol-5-yl, $NH_2SO_2CF_3$, $SO_2NHCO$-phenyl, $SO_2NHCO$-cyclopropyl, L is a linker moiety or a bond, and R is a moiety detectable in in vivo imaging of a human or animal body.

2. A method of generating an image of an animate human or non-human animal subject involving administering a contrast agent to said subject and generating an image of at least a part of said subject to which said contrast agent has distributed, characterised in that as said contrast agent is used a composition of matter of formula I as defined in claim 1.

3. A method as claimed in claim 2 wherein said image is a nuclear imaging image.

4. A method as claimed in claim 2 wherein said image is an ultrasound image.

5. A pharmaceutical composition comprising a composition of matter of formula I as defined in claim 1 together with at least one pharmaceutically effective carrier or excipient.

* * * * *

SEQUENCE LISTING

```
<160> NUMBER OF SEQ ID NOS: 1

<210> SEQ ID NO 1
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION:
<220> FEATURE:
<221> NAME/KEY: PEPTIDE
<222> LOCATION: (1)..(8)
<223> OTHER INFORMATION: Angiotensin II peptide

<400> SEQUENCE: 1

Asp Arg Val Tyr Ile His Pro Phe
1               5
```